US009161884B2

(12) United States Patent
Barlow et al.

(10) Patent No.: US 9,161,884 B2
(45) Date of Patent: Oct. 20, 2015

(54) PROCESS FOR PROVIDING A QUANTITY OF A PARTICULATE MATERIAL, PRODUCT AND APPARATUS

(75) Inventors: Stephen Barlow, Harlow (GB); Howard Biddle, St. Ives (GB); Roderick Haines, St. Ives (GB); Keith Smith, Harlow (GB)

(73) Assignee: Glaxo Group Limited, Brentford, Middlesex (GB)

( * ) Notice: Subject to any disclaimer, the term of this patent is extended or adjusted under 35 U.S.C. 154(b) by 1154 days.

(21) Appl. No.: 12/520,098

(22) PCT Filed: Dec. 17, 2007

(86) PCT No.: PCT/EP2007/064083
§ 371 (c)(1), (2), (4) Date: Jun. 19, 2009

(87) PCT Pub. No.: WO2008/074784
PCT Pub. Date: Jun. 26, 2008

(65) Prior Publication Data

US 2010/0068246 A1 Mar. 18, 2010

(30) Foreign Application Priority Data

Dec. 19, 2006 (GB) .................................. 0625275.3

(51) Int. Cl.
*A61K 9/70* (2006.01)
*A61J 3/00* (2006.01)
*A61J 3/10* (2006.01)

(52) U.S. Cl.
CPC ..... *A61J 3/00* (2013.01); *A61J 3/10* (2013.01); *Y10T 156/1092* (2015.01); *Y10T 156/1712* (2015.01); *Y10T 156/1744* (2015.01)

(58) Field of Classification Search
CPC .......................................................... A61J 3/00
See application file for complete search history.

(56) References Cited

U.S. PATENT DOCUMENTS

| | | | | |
|---|---|---|---|---|
| 4,029,757 | A * | 6/1977 | Mlodozeniec et al. | 424/452 |
| 4,699,792 | A * | 10/1987 | Nick et al. | 424/446 |
| 5,723,145 | A * | 3/1998 | Shikinami et al. | 424/448 |
| 5,958,447 | A * | 9/1999 | Haralambopoulos et al. | 424/449 |
| 2003/0012926 | A1 | 1/2003 | Murari et al. | |
| 2006/0041248 | A1 | 2/2006 | Patton et al. | |
| 2008/0095477 | A1 * | 4/2008 | Hagino | 383/200 |

FOREIGN PATENT DOCUMENTS

| | | |
|---|---|---|
| EP | 0 721 024 | 7/1996 |

* cited by examiner

*Primary Examiner* — Jake Vu
(74) *Attorney, Agent, or Firm* — Joshua C. Sanders; Theodore R. Furman

(57) ABSTRACT

A process for providing a predetermined quantity of a particulate material in which the particulate material is deposited on a defined area of a sticky surface of a substrate. The process is suitable for deposition of particulate drug material on a substrate such as a strip form substrate which can then be compacted to provide a delivery device for delivering the predetermined quantity of the particulate material. Such a delivery device, and an apparatus to perform the process, comprise further aspects of the invention.

13 Claims, 12 Drawing Sheets

Cumulative variation from mean (SB 659032)

PROCESS FOR PROVIDING A QUANTITY OF A PARTICULATE MATERIAL, PRODUCT AND APPARATUS

This application is a 371 of International Application No. PCT/EP07/64083, filed 17 Dec. 2007, which claims the priority of GB Application No. 0625275.3, filed 19 Dec. 2006, which are incorporated herein in their entirety.

This invention relates to a novel process for providing a predetermined quantity of a particulate material, to products made using this process, and to apparatus for performing the process. In particular the invention relates to a process, product and apparatus in which the particulate material is a drug substance.

In many technical fields it is necessary to provide predetermined, relatively small, quantities of particulate material within narrowly defined limits of weight consistency, for example for further processing to provide a device containing, using or delivering the material. Examples of such technical fields include flavouring, where a small quantity of a flavouring agent may need to be added to a mixture of edible materials, explosives, and in particular the pharmaceutical industry in which small quantities of medicinally active materials (herein termed "drug substance", this term including any kind of medicinally active material, including chemical compounds, biological materials, vaccines and formulations comprising such materials, and placebo substances e.g. as used in clinical trials) are incorporated into delivery devices for administration to the human or animal body.

In the pharmaceutical industry numerous types of drug delivery device are known. Common forms of drug delivery devices are compacted tablets and capsules. Such devices suffer from the problem of mixing relatively small quantities of drug substance into a large quantity of bulk powder or granules comprising fillers, excipients etc. with sufficient uniformity that when the mixture is subdivided into amounts suitable for a tablet or capsule the drug substance therein is uniformly distributed into each individual dosage form. This is particularly a problem with more active drug substances which are used in smaller quantities.

Methods are known for depositing drug substance onto the surface of substrates to produce dosage forms. U.S. Pat. No. 4,029,757 discloses a drug delivery device in which a drug substance is deposited onto an edible web, and the web is then subdivided and compacted e.g. by folding, then encapsulated, to form a compact dosage form. In this disclosure the drug substance is preferably deposited in powder form electrostatically onto the web and to enhance the adherence of the material onto the web an adherence enhancing material such as carboxymethylcellulose or methylcellulose may be applied to the web. The powder deposition method disclosed in U.S. Pat. No. 4,029,757 comprises powder cloud electrostatic deposition. GB-A-2 370 243 discloses a drug delivery device comprising a solid compacted dosage form onto the surface of which a drug substance is deposited electrostatically. U.S. Pat. No. 6,804,313 also discloses a drug delivery device in which a drug substance powder is deposited electrostatically upon predefined regions of a substrate.

An important requirement in the above-mentioned fields is the consistent provision of predetermined quantities of the particulate material, e.g. to achieve a consistent strength of flavour when using a particulate flavouring material. Significant deviation from consistency with a drug substance can have disastrous consequences. It is difficult to achieve consistency with powder cloud electrostatic deposition processes. It is an object of this invention to address the problem of providing consistent and precise quantities of particulate substances in particular of drug substances, especially for the purpose of incorporating the drug substance so provided into a drug delivery device.

According to a first aspect, this invention provides a process for providing a quantity of a particulate material comprising:

providing a substrate having a sticky surface, bringing the particulate material into contact with the sticky surface so that particulate material becomes stuck to the sticky surface, removing excess particulate material from the substrate which has not become stuck thereto, and forming a unit of the substrate comprising an area of the sticky surface having the particulate material stuck thereto.

In a preferred embodiment this invention provides a process for the preparation of a drug delivery device, comprising:

providing a substrate having a sticky surface, bringing a particulate material being a drug substance into contact with the sticky surface area so that particulate material becomes stuck to the sticky surface, and removing excess particulate material from the substrate which has not become stuck thereto, forming a unit of the substrate comprising an area of the sticky surface having the particulate material stuck thereto, then further processing the unit of substrate into a form suitable as a drug substance delivery device.

The term "drug substance" as used herein includes curative and preventative substances, and placebos.

The invention is based on the unexpected discovery that a density per unit area of the particulate material can be achieved on the sticky surface which is sufficiently uniform that the quantity of particulate material can be consistently related to the area of the sticky surface, such that the quantity of particulate material stuck thereon can be predetermined with considerable accuracy. Therefore by isolating a defined area of the sticky surface, a defined quantity of the particulate material can be consistently provided, e.g. as a unit dose or fraction of a unit dose of a drug substance.

The physical form of the substrate may be selected to be appropriate for the application for which the particulate material is intended.

By "sticky" herein is included that particles coming into contact with the surface area are retained therein against forces, e.g. gravitational forces, tending to remove them. The sticky surface area may be sticky as an inherent property of the material of which the substrate is made, and such inherent stickiness may be enhanced by appropriate treatment. Alternatively the sticky surface area may be provided by means of a substrate base which has its surface made sticky by surface treatment, e.g. with energy such as heat, or treatment e.g. with chemicals, organic solvent or water, or by application of a sticky single- or multi-layer coating of sticky substance to the surface of a substrate base. "Sticky" herein also includes known include microsurfaces utilising short range forces such as van de Waals forces to cause adhesion thereto, for example surfaces covered with micro hairs to create intimate surface contact.

For example the substrate may be in the form of a thin film, even a monomolecular layer film (provided this can be made sufficiently robust or supported for any necessary subsequent further processing), a fibre, or a hollow bubble which for example may have the particulate material applied to its outer sticky surface, then optionally collapsed.

The substrate may for example comprise a mass of an inherently sticky substance.

One form of substrate may comprise a rigid solid article, e.g. of compacted ingredients, having a sticky surface over all or part of its outer surface. Such a substrate may for example be suitable for particulate materials which are flavouring materials, such that the substrate plus particulate material may be added to a foodstuff. In this case the article should be made of edible materials.

A substrate in the form of such a rigid solid article may also be suitable when the particulate material is a drug substance, so that the substrate with its stuck-on particulate material is a drug delivery device. Such a substrate may be in the form of a solid article shaped for introduction orally or otherwise to the human or animal body, and having a sticky surface over all or part of its surface area. Such an article may for example comprise a substrate base in the form of a compacted tablet, typically made from the same excipients such as filler, lubricant, disintegrating agent etc. as commonly used in the pharmaceutical industry. In this case the article should be made of materials which are medicinally acceptable, e.g. edible.

A preferred form of substrate comprises a sheet-form flexible material having a sticky surface area, either as an inherently sticky substance or as a substrate base having a sticky substance applied thereto.

Such a sheet-form flexible material should be of a thickness and flexibility which facilitates its further processing into a desired form for a dosage form, e.g. an oral dosage form. This further processing may be by for example folding or rolling to thereby enclose the particulate material within the further-processed substrate such that the particulate material is not exposed to the outside environment. Such folding or rolling can also make the folded or rolled substrate more compact than the original unfolded substrate. Such a sheet-form flexible material is suitable when the particulate material is a drug substance, to facilitate further processing to compact the substrate into a shape and size appropriate for a drug delivery device. The thickness of such a sheet-form substrate for such applications may be determined by practical considerations e.g. handling the substrate. For example thicknesses may be in the range 20-100 microns. Typically such a sheet-form substrate may be in elongate strip form. The surface of such a sheet-form substrate, e.g. the sticky surface, is preferably flat.

Preferably the substrate is a material that does not tend to build up a charge of static electricity, as such charges can tend to cause retention of powdered drug substance of areas of the substrate other than the sticky surface area. Preferred substrate materials are dimensionally and mass stable, e.g. they do not tend to stretch or bow during the forces experienced during the process. For example the substrate material may be fibre-reinforced. The substrate should also be easy to cut or otherwise subdivide for example during further processing. The substrate may be anisotropic, i.e. having different properties, e.g. strength, in different directions.

For applications which involve administration to the human or animal body the substrate must be made of a material which is non-toxic. The substrate may be degradable within the body of a human or animal patient e.g. by disintegration, dissolution, digestion etc. The substrate may alternatively be inert within the body of a human or animal patient such that it passes inertly through the digestive tract. Possible examples of edible materials from which a sheet-form substrate base may be made include alginates, carrageen, whey, casin, starch, collagen, gelatin, rice protein and other vegetable-based sheets. Suitable materials include the sheet-forming materials disclosed in U.S. Pat. No. 4,029,757, for example natural and modified starches and dextrins, proteins such as gelatin, cellulose derivatives such as sodium carboxymethyl cellulose, hydroxypropylmethyl cellulose, hydroxyethylcellulose, polysaccharides such as pectin, acacia xanthan gum, guar gum, algin, synthetic materials such as polyvinylpyrrolidone and polyvinyl alcohol. Numerous forms of such materials are known to be "GRAS" (Generally regarded as safe) e.g. for oral ingestion or for administration to the body in other ways. Such materials can degrade within the human or animal body in various ways, e.g. by dissolution, disintegration, digestion, becoming porous etc.

A suitable material for use as a sheet-form edible substrate suitable for an oral dosage form is hydroxypropylmethyl cellulose ("HPMC"). A suitable sheet-form of such an HPMC material is available from Monosol Ltd. (GB).

For use as a substrate it may be useful for the substrate to be able to store energy, e.g. may be resilient so that if the substrate is folded or rolled into a compacted form and constrained in this form, when the constraint is released the substrate spontaneously unfolds or unrolls to increase its surface area and to expose the particulate material thereon. This may be useful for substrates intended as drug delivery devices. Such constraint may for example be by encapsulation or embedding within a compacted tablet, and the release of constraint may for example be by a subsequent disintegration etc. of the tablet or capsule. For use as a substrate for a drug delivery device the substrate may also be used to control the release rate of the drug substance, e.g. a slow-dissolving substrate may be used, or the point in the digestive system where the drug substance is released may be controlled. For example the dissolution or disintegration rate of the substrate material in the gastric environment can control the rate of release of the drug substance in the gastric environment. For example the relative solubility of the substrate in gastric environments of different pH can be used to determine where in the digestive tract a drug substance thereon is released.

Various sticky substances may be applied to a substrate base, such as a sheet-form substrate base. Contact or pressure sensitive sticky coatings are preferred, edible ones of which are known. Alternatively the sticky area may become sticky when its temperature is increased, for example a so called "hot melt" adhesive may be used, e.g. waxes and resins. However such a hot melt adhesive should have a working temperature which is tolerable by the particulate material such as a drug substance deposited thereon. Any layer of sticky substance should preferably be uniform, i.e. with no gaps, and level, i.e. non-ridged. Suitable sticky substances which are GRAS will be apparent to those skilled in the art, e.g. based on sugars and organic acids, rice-based adhesives, natural gums and latexes etc. In the case of particulate materials which are drug substances the sticky substance must be compatible with the drug substance.

The sticky surface may extend over the entire surface of the substrate, e.g. over all of one or both opposite surfaces of a sheet-form substrate. Alternatively the sticky surface may extend over only part of the surface of the substrate, e.g. over all or part of one or both opposite surfaces of a sheet-form substrate base, or e.g. as a sticky patch on part of the surface of a rigid solid article such as a compacted tablet for use as a drug delivery device. When the sticky surface extends over only part of the surface of the substrate, the sticky surface may for example comprise patches or stripes upon the surface of the substrate. For example such patches or strips may be bordered or surrounded by areas of non-sticky surface. Such patches or stripes, and the areas of non-sticky surface adjacent to them may comprise shapes which facilitate further processing. For example in the case of sheet-form substrates the shape, size and position of such patches or stripes can facilitate subsequent folding or rolling, and/or subdividing the substrate in places between the sticky areas, and/or retaining the further processed substrate in its further processed, e.g. rolled or folded form. An example of such a shape is a cross shape, so that the limbs of the cross may be folded onto or across the part of the cross where the limbs meet.

The extent of the substrate over which the sticky surface area extends, and/or its stickiness e.g. the weight per unit area of the particulate material with which the sticky surface area can be loaded and retained against gravitational force, will depend upon the intended application and can be determined empirically. The sticky surface area can facilitate the further processing for example in the case of a sheet-form substrate by causing the substrate to stick together to thereby retain the substrate in the further processed state, e.g. to resist for example unfolding or unrolling.

The substrate with its sticky surface area may be prepared in various ways.

When the substrate comprises an inherently sticky substance having an inherently sticky surface, a mass of such an inherently sticky substance may be prepared in various ways. For example a substrate in the form of a thin sheet of an inherently sticky substance may be provided by known film-forming techniques e.g. depositing the substance on a water surface and allowing it to spread to form a thin layer which can be lifted off for use. Hollow bubbles may be prepared by known bubble-blowing techniques.

For example a mass of a sticky substrate may be deposited upon a release carrier from which it can subsequently be peeled. A suitable form of release carrier is a sheet-form flexible material. Masses of sticky material of other forms e.g. fibres may be provided in other generally known ways.

When the substrate comprises a substrate base having a sticky substance deposited on all or part of its surface this may be prepared in various ways.

A substrate comprising a fibre or a rigid solid article, e.g. of compacted ingredients, having a sticky surface over all or part of its outer surface, may be prepared by generally known techniques e.g. printing, spraying the article with or dipping the article in, a fluid sticky substance.

The preferred form of substrate comprising a substrate base being a sheet-form flexible material having a sticky substance on its surface may also be prepared from an initial sheet-form flexible material without any sticky surface, and a sticky surface may be applied to a surface thereof, using generally known techniques e.g. casting onto the surface optionally with known treatments such as curing, drying etc., pre-casting onto a release liner and transferring the sticky coating to the substrate, or screen printing, spraying the sheet-form material with, or dipping the sheet-form material into, a fluid sticky substance. For the application of stripes conventional slot or roller coating may be used. For the application of patches conventional printing processes may be used, e.g. screen printing. The sticky surface of the substrate may be protected by a protective peel-off release film which may be removed prior to use.

A preferred sticky substance is a mixture of glyerine:gelatine:water, suitably in a weight ratio 2-3:2-4:1, preferably 2.4+/−0.1:3+/−0.1:1. This mixture may be blended by mixing and heating in a conventional manner until the mixture is fluid, and may be applied in a fluid state to the substrate. On cooling, and the evaporation of the water content that is likely to occur, this mixture results in a sticky mass. Alternatively this mixture can be fluidized by heat and cast or compressed e.g. between sheets of a release film, themselves located between rollers to form a thin solid layer. On cooling this thin layer of sticky substance can be isolated e.g. by peeling it off from a release film and then attaching it by means of its stickiness to the substrate. This sticky substance advantageously is made entirely of edible food grade materials, has been found to result in a suitable dosing of particulate material, and is transferable to edible substrates to give a soluble product.

The thickness of such a layer of sticky substance does not appear to be critical for suitable adhesion of the particulate materially. In practice layers 10-150 microns thick may be suitable, e.g. typically 50-100 microns thick should suffice.

The substrate may be provided for the step of bringing the particulate material into contact with its sticky surface in a way which is appropriate to the physical form of the substrate. For example substrates which are in the form of a mass of a sticky substrate on a release carrier comprising a sheet-form flexible material, or the preferred form of substrate comprising a substrate base being a sheet-form flexible material having a sticky substance on its surface, may be provided by generally conventional means such as rollers, guides, conveyors etc., adapted to feed the sheet-form substrate in a conventional manner.

The present invention appears to be suitable for any kind of particulate material, and ways of providing different types of particulate materials to bring them into contact with the sticky surface will be apparent to those skilled in the art. The process appears to be suitable for the three commonly encountered types of particulate material: dry clumping (which form clumps when agitated but the clumps break apart easily), free running (non-clumping and which pour easily), and sticky clumping (which form clumps and ball when agitated and the clumps do not easily break up). In the case of drug substances, the method and delivery device of the present invention appears to be suitable for any type of particulate drug substance, including particles of pure active(s) and particles of formulations comprising one or more active, together with the usual substances, excipients etc. used in the pharmaceutical art to make up drug formulations. The amount of particulate material adhering in practice to the sticky substance may be dependent upon the particulate material. For example using particulate lactose in micronised, clumping and free running grades, loadings of respectively 0.1, 1.6 and 5.4 $mg/cm^2$ could be achieved. Similar loadings of other particulate materials are believed to be possible.

The process of the invention appears to be suitable for particulate material over a range of particle sizes.

Particle sizes in the range 0.5-250, for example 5-100 microns appear to be suitable both generally and for particulate drug substances. A suitable particle size of particulate drug substance for use in the present invention may also depend upon the drug substance and the intended application and may be determined by experiment. Micronised powder particles may be suitable. The quantity of the particulate material to be stuck onto the sticky surface area will of course depend on the intended application of the material. In the case of drug substances for use as a drug delivery device, quantities corresponding to a unit dose of the drug substance, or a fraction of a unit dose, may be stuck onto the sticky surface. When the quantity of drug substance stuck to the sticky surface comprises a fraction of a unit dose a unit dose may be delivered by using a suitable multiple of units of the substrate with their drug substance stuck on.

Bringing the particulate material into contact with the sticky surface area so that particulate material becomes stuck to the sticky surface may be performed in various ways.

For example the particulate material may be caused to fall by gravity onto the sticky surface, preferably passing the particulate material through a sieve. Such a sieve may control the size of particles of the particulate material which become stuck to the sticky surface, may break up agglomerates of the particulate material, and may control the rate at which the particulate material reaches the sticky surface. Such a sieve may be vibrated to assist the flow of particulate material through the sieve, one mode of vibration being vibratory motion in the direction in which the particulate material passes through the sieve. However high frequency vibration may cause undesirable clumping of the particulate material and a suitable frequency can be found experimentally. Such a sieve may be planar, but a curved sieve, convex on the downstream side, has been found to assist in centering the flow of the particulate material toward the sticky surface. Such a sieve should be larger than the area of sticky surface into contact with which the particulate material is to be brought to ensure full coverage of the area.

For example the particulate material may be provided in a generally conventional hopper means, with a lower particulate material dispensing opening, which may be provided with such a sieve.

Alternatively for example the particulate material may be directed toward the sticky surface in a stream of air or an air-supported cloud of the particulate material.

Alternatively for example particulate material may be provided from the output of a source of particulate material, such as a micronizer, cyclone, fluidised bed (e.g. a drier) or spray drier, as commonly used in the preparation of particulate drug substances. The substrate may be agitated to encourage even distribution of the particulate material over the sticky surface.

Alternatively for example particulate material may be brushed over the sticky surface via a soft brush, e.g. a so-called fingerprint brush.

A suitable depth of particulate material is for example one in which all of the particles of the particulate material are in contact with the sticky surface and so are held entirely or primarily by the sticky surface, rather than by interactions between the particles themselves which may occur.

Forming a unit of the substrate comprising an area of the sticky surface having the particulate material stuck thereto has the effect of isolating a quantity of the particulate material of a known quantity, based upon the quantity of the particulate material stuck to the area of sticky surface upon the unit, which may be determined empirically. As it has been unexpectedly found that the method of the invention results in a substantially uniform density of the particulate material per unit area of sticky surface, the amount of particulate material can be directly related to the area of the sticky surface.

Such a unit of the substrate may be formed in various ways.

For example the area of sticky surface may itself be divided to thereby form such isolated units of the sticky surface.

However it is preferred to provide a unit of the substrate comprising a defined area of the sticky surface before the particulate material is stuck thereto. This can be achieved in various ways.

For example the unit of substrate may comprise the entire substrate, and the defined area may be the entire sticky surface area.

For example when the substrate comprises a rigid article such as a compacted tablet, each such article may comprise a unit having a defined area of sticky surface thereon, for example covering the whole or part of the surface of the article, e.g. a patch of sticky substance occupying a defined part of the surface of the article.

For example when the substrate comprises a mass of a sticky substrate deposited upon a release carrier from which it can subsequently be peeled, the particulate substance may be brought into contact with all or part of the surface area of this sticky mass, then subsequently the mass together with the particulate material stuck thereon may be peeled as a unit from the release carrier.

For example the substrate may have a surface which may be made locally sticky, e.g. comprising a substrate base with a surface coating of which a defined area can be locally treated e.g. by heat, radiation, chemical treatment etc. to render the defined area sticky, and this defined area may comprise the unit of substrate.

For example the substrate may be sub-divided to form the units of substrate.

For example when the substrate comprises a substrate base being a sheet-form flexible material having a sticky substance on its surface, forming the unit of the substrate comprising a defined area of the sticky surface may be achieved by locating the sticky substance in discrete area units on the substrate. This may be done in various ways.

In one way with such a substrate the sticky substance may be located on the substrate base in discrete patches of any desired shape (e.g. rounded, rectangular, elongated stripes etc.), isolated from each other by areas of the surface of the substrate base without any sticky substance thereon.

In another way with such a substrate the sticky substance may be located on all or part of the surface of the substrate base e.g. in patches thereon, and a region of the sticky surface may be isolated by positioning a mask adjacent thereto, the mask having one or more aperture through which the particulate material may pass and come into contact with the region of the sticky surface defined by the aperture. In such a way the unit of the substrate isolated from other units of the substrate and comprising a defined area of the sticky surface is provided before the particulate material is applied thereto. The aperture of such a mask defines the area of the sticky surface into contact with which the particulate material comes.

Such a mask may be made of a material such as metal or a plastics material which is compatible with the particulate material, such as a drug substance. A suitable material is stainless steel. Flexible materials may also be used for the mask allowing distortion of the mask to alter the size of the aperture, and/or the edges of the aperture may be otherwise moveable to allow adjustment of the size and/or shape of the aperture. Typically the mask comprises a sheet form of the material having opposite facing surfaces with the aperture passing through the thickness of the material. Preferably such a sheet is thin to avoid excessive build up of depth of the particulate material. The shape and dimensions of the aperture will depend upon the intended application. The amount of particulate material which is required to pass through the aperture can be determined empirically. For example, in the case of particulate materials which are drug substances, on a loading of 1.0 mg/cm$^2$, to achieve a loading of 50 mg of the drug substance an area of the aperture of ca. 50 cm$^2$ may be needed.

The aperture may be of any convenient shape e.g. rounded e.g. circular, or polygonal e.g. rectangular or square. Rounded apertures, e.g. rectangular apertures with rounded corners may help to avoid any build up of particulate material in sharp corners. A circular aperture is convenient. The profile of the edge of the aperture may be selected experimentally to avoid build up of particulate material at the edges of the aperture. For example right-angled, chamfered or curved edge profiles may be suitable for different types of particulate material.

The mask may be positioned adjacent to the sticky surface by causing the sticky surface to stick to the mask so that the substrate is in sticking contact with the mask. This can help to seal the perimeter of the aperture to the sticky surface. For such an application preferably the sticky surface, e.g. a sticky substance, and the mask are capable of being easily peeled relatively apart. Preferably the sticky surface, e.g. a sticky substance, is of a type which leaves no sticky residue on the mask when the substrate is peeled from the mask.

Positioning such a mask and the substrate adjacent to each other may be achieved in various ways.

For example a mask may be provided, and the substrate and the mask may be relatively moved into position adjacent to, preferably in contact with, each other, the particulate material may be allowed to pass through the aperture so as to be brought into contact with the sticky substance, excess particulate material may then be removed, then the mask and substrate may be separated from each other. The mask may then be re-used, preferably after cleaning to remove excess particulate material and/or sticky substance deposits. A suitable form of mask for a sheet form substrate is a hollow cylinder of circular or polygonal section having one or plural apertures through its wall and around which the substrate can be wound in sticking contact.

For example a substrate, e.g. a substrate in the form of a rigid article or flexible sheet-form substrate base with a sticky substance on a surface, may be provided with a film-form mask adjacent to its surface, e.g. stuck to the surface by means of the sticky substance, and having one or more aperture therein exposing corresponding regions of the sticky substance via the aperture(s). The particulate material may be brought into contact with the sticky substance via the apertures, excess particulate material may then be removed, then the film-form mask and substrate may be separated from each other, e.g. the film-form mask may be peeled from the substrate.

Forming a unit of the substrate, especially to provide a delivery device for the particulate material such as a drug delivery device, may comprise sub-division of the substrate to isolate area units of the sticky substance with particulate material stuck thereon. This may be done with a sheet-form substrate having a sticky surface by cutting the substrate to isolate one or more defined area of the sticky surface having the particulate material stuck thereto. Such cutting is preferably through areas of the substrate which have no sticky substance thereon.

In one form of the process of the invention such a substrate may be in the form of an elongate strip, and plural patches of the sticky surface may be disposed across the width of the strip, and/or disposed along the length of the strip. Such an elongate strip may be subsequently subdivided into units including a defined number or part of such patch(es), e.g. only one, patch or part of a patch. Such cutting may for example be by means of laser cutting or cutting knives operating along the length or across the width of such a sheet, or by a closed blade, of the "pastry cutter" type, stamping out areas of the substrate. The presence of regions of the substrate without any sticky substance thereon, between patches of sticky substance on a sheet-form substrate facilitate the dividing of the web into units, in that the substrate can be cut through these sticky substance-free regions without contacting the sticky substance. This can help to avoid contamination of any cutting knife with the sticky substance. Such a substrate may be provided with areas e.g. lines of weakness to facilitate such sub-division.

Excess particulate material which has not become stuck to the sticky surface may be removed from the substrate surface in various ways.

For example the substrate may be positioned so that the sticky surface is facing downwards and gravity can cause excess particulate material to fall from the substrate.

For example a stream of air may be blown across the sticky surface to blow away excess particulate material.

For example excess particulate material may be brushed away with a gentle brush.

For example the substrate may be vibrated or otherwise agitated to encourage excess particulate material to leave the substrate surface.

For example the substrate with the particulate material deposited thereon, with particulate material stuck onto the sticky surface and some excess particulate material may be oriented so that the sticky surface is downwards, then the opposite surface to the sticky surface may be gently tapped e.g. with a solenoid operated tapper. The sharpness of tapping to cause excess particulate material to fall away from the substrate may be determined experimentally.

Combinations of two or more of these foregoing may be used.

If the above-described mask is used then excess particulate material should be removed before the mask and substrate are moved out of their adjacent position, otherwise excess particulate material on the mask might undesirably become scattered onto regions of the sticky surface previously covered by the mask. The mask may be made of a material, or have a surface coating, which hinders the retention of the particulate material on the mask. and also prevents the adhesive leaving a residue on the mask In a preferred form of the process of the invention the substrate is of flexible sheet form, as described above, is in the form of an elongate strip form, and is provided for the process of the invention by being fed continuously along its length direction into a position adjacent a mask, suitably the cylindrical mask as described above. In this preferred form the particulate material is brought into contact with the sticky surface, excess particulate material is removed from the substrate, the substrate is then moved apart from the mask, then the substrate is subdivided to isolate one or more unit of the substrate each comprising a defined area of the sticky surface with the particulate material.

Such units of the substrate may be further processed to suit any particular application.

For example the particulate material stuck onto the sticky surface may be covered with a protective cover layer, e.g. a protective film.

For example a sheet-form substrate, e.g. in the form of an elongate strip, may be compacted. Compaction of such a sheet-form substrate may for example by rolling (with or without a core) into a cylinder, folding (e.g. book-form, concertina form etc.), or isolated units may be stacked, to compact the substrate into a smaller form.

For example a compacted sheet-form substrate may then be enclosed or encapsulated in a suitable carrier such as a compacted tablet or capsule. Methods of doing so are well known in the art. Such a compacted tablet or capsule may comprise a drug delivery device of a shape and size suitable to administer the device to the human or animal body, typically the shape and size of a conventional pharmaceutical tablet or capsule or suppository etc.

The process of the invention may also comprise measuring the amount of particulate material which has become stuck onto the sticky surface. Such measurement may be applied to all of the particulate material stuck on the sticky surface or to representative samples of the particulate material, e.g. to representative samples of the sticky surface. Suitable measurement techniques include optical methods e.g. image processing, light scatter, transparency, shadow graph, laser scanning and spectrometry of various kinds. Other techniques include ultrasonic measurement, use of beta particle radiation, X-ray fluorescence, capacitance measurement, measurement of the effect of the mass of the particulate material on the vibration resonance frequency. Alternative techniques include weight measurement and analytical chemistry. Such measurement may be used to provide feedback to control the process, e.g. to control the rate of delivery of particulate material, the size of the aperture etc. Apparatus of the invention may comprise means to perform such measurement and to apply such measurements to control of the apparatus.

In a further aspect of this invention, a delivery device is provided for delivering a particulate material comprises a substrate having a sticky surface, and having a particulate material stuck thereto.

In particular, the delivery device is for delivering a defined quantity of a particulate material being a drug substance, and comprises a substrate having a sticky surface, and having a particulate material being a drug substance stuck thereto.

Preferably a defined quantity of the particulate material is stuck to the sticky surface. For example in the case of a particulate material which is a drug substance this defined quantity may comprise a unit dose or a defined fraction of a unit dose e.g. half, a third, a quarter or a fifth etc.

Suitable and preferred features of the substrate, sticky substance and particulate material are as described above with reference to the first aspect of the invention, viz. the above-described process. The delivery device of this aspect of the invention may be prepared by the above process.

Therefore one form of drug delivery device of the invention comprises a sheet-form substrate having a sticky surface area thereon, a particulate material, such as a drug substance stuck to the sticky surface area, the substrate being folded, or being rolled into a cylinder to enclose the particulate drug substance within the folded or rolled substrate. Preferably adjacent folded or rolled areas of the substrate are stuck together by the sticky surface.

The drug delivery device of the invention may comprise such a sheet-form substrate having a sticky surface area thereon, a predetermined amount of a particulate drug substance stuck to the sticky surface area, the substrate being encapsulated within a capsule, or embedded within a compacted tablet. In this drug delivery device the substrate may be in the above-mentioned compacted, e.g. folded or rolled, form.

A delivery device of this aspect of the invention may comprise one or more particulate material, e.g. a drug delivery device of this invention may comprise two or more drug substances. For example two or more sheet-form substrates with corresponding respective two or more particulate drug substances stuck thereto may be laminated together, and then the laminate may be further processed e.g. folded or rolled as above, then encapsulated or embedded. Alternatively two or more sheet-form substrates with corresponding respective two or more particulate drug substances stuck thereto may be further processed e.g. folded or rolled as above, then encapsulated or embedded together. Two or more substrates in such drug delivery devices may provide different release rates of their respective drug substances.

A principal advantage of the present invention is the consistency in the weight of a particulate substance, especially a drug substance, that it appears can be deposited on the sticky surface. For example variation of +/−2.5% by weight in the amount of drug substance deposited appears to be feasible, possibly less variation on optimisation.

According to a third aspect of this invention an apparatus for performing the process of the invention comprises:

means to provide a substrate having a sticky surface to a location where a particulate material may be brought into contact with the sticky surface area so that particulate material becomes stuck to the sticky surface, means to bring the particulate material into contact with the sticky surface area so that particulate material becomes stuck to the sticky surface, means to remove excess particulate material from the substrate which has not become stuck thereto.

Suitably the apparatus comprises means to isolate areas of the sticky surface from other areas of the sticky surface and to bring particulate material into contact with the isolated areas of sticky surface area so that particulate material becomes stuck thereto.

Suitably the apparatus comprises means to divide such one or plural areas of sticky surface from such another area. Such means may comprise means to divide the substrate into divided parts comprising such one or plural areas of sticky surface. For example such means may be adapted to cut a substrate being of a sheet or elongated strip form.

Optionally the apparatus may comprise further processing means to process the substrate into a form suitable for administration to the human body. Such means may comprise means to compact a sheet form or elongate strip-form substrate or divided parts thereof and encapsulate these.

The apparatus may be suitable to produce a delivery device, such as a drug delivery device, according to the second aspect of the invention.

Suitable and preferred details of the substrate, particulate material, sticky surface, etc. are as described above.

In this apparatus the means to provide a substrate may for example comprise a support for the substrate and means to feed the substrate toward the means to bring the particulate material into contact with the sticky surface. For a substrate in the form of an elongate strip such means may comprise one or more generally conventional feed roller and/or one or more conveyor upon which the strip may be laid.

The means to provide a substrate may also comprise means to apply a sticky substance to the substrate, for example a generally conventional slot roller or roller coating means, or a conventional printing means such as a screen printing means.

If the sticky surface has been protected prior to use in the apparatus e.g. by a peel-off cover as mentioned above, the apparatus may also comprise a generally conventional means to remove such a protection e.g. cover prior to bringing a particulate material into contact with the sticky surface, e.g. before positioning of the substrate adjacent to a mask. Such means are generally suitable for a sheet form substrate.

The means to bring the particulate material into contact with the sticky surface may incorporate a mask as described above. In one embodiment such a mask may comprise a rotatable drum bounded by a drum wall, suitably a hollow cylindrical or polygonal-section drum and having one or plural apertures through the wall of the drum such that the wall of the drum and the aperture(s) comprises the mask. For example the drum may be suitable to wind a sheet-form substrate around the outer surface of the drum. The sticky surface of the substrate may be in sticky contact with the outer surface of such a drum such that the sticky surface is exposed to the interior of the drum through the aperture(s). The dimensions of the apertures define the area of the substrate which is exposed to the particulate material therethrough. One form of such a drum construction comprises two concentric drums being an inner drum provided with relatively large apertures therein, over which is located an outer drum provided with relatively smaller apertures therein, these relatively smaller apertures determining the area of the sticky surface exposed to the particulate material therethrough. In such a construction the outer drum may be removable from, replaceable on and supported by the inner drum. By this construction replaceable outer drums may be used having different sizes, shapes or positions of apertures.

In such an embodiment, within such a drum there may be a source of the particulate material. Suitably this source may be configured to cause the particulate material to fall downwards toward the sticky surface. Such a source may comprise a hopper with a lower dispensing opening, preferably provided with a sieve, through which particulate material may fall under gravity toward one or more aperture of the drum.

In such an embodiment the drum may be rotated to bring one or more aperture into a position beneath the source so that particulate material falls toward an aperture beneath the source, passes through the aperture onto the sticky surface exposed to the interior of the drum through the aperture and becomes stuck to the sticky surface. Thereafter rotation of the drum may move the aperture(s) away from a position beneath the source, for example into a position above the source, so that excess particulate material falls away from the substrate, for example back into the source. In such a construction it has been found advantageous for the drum to be of such a thickness that the sides of the aperture(s) through the drum wall provides pockets in which excess particulate material which is not stuck to the sticky surface may sit as the drum rotates. In this way unwanted tumbling of the excess particulate material within the drum as the drum rotates can be reduced. Thereafter rotation of the drum may move the substrate into a position from which the substrate may be removed from sticky contact with the drum. The removal of such a substrate from its sticking contact with the drum may for example be by means of a generally conventional take-off roller.

Consequently a form of the apparatus of the invention incorporating these preferred features comprises:

means to provide an elongate strip-form substrate comprising a support for the substrate and means to feed the substrate toward the means to bring the particulate material into contact with the sticky surface of the strip form substrate, a means to bring the particulate material into contact with the sticky surface comprising a rotatable drum bounded by a drum wall and having one or plural apertures through the wall of the drum such that the wall of the drum and the aperture(s) comprises a mask, the aperture defining the area of the sticky surface to be exposed to the particulate material, and around the outer surface of which drum the substrate may be wound such that the sticky surface is exposed through the one or plural apertures, within the drum being a source of the particulate material adapted to dispense the particulate material such that it passes through an aperture and comes into contact with the sticky surface exposed therethrough, the drum being rotatable to bring one or more aperture into a position adjacent the source so that particulate material from the source passes through the aperture onto the sticky surface exposed to the interior of the drum through the aperture and becomes stuck to the sticky surface, the drum being thereafter rotatable to move the aperture(s) away from a position adjacent to the source such that excess particulate material falls away from the substrate, the drum being thereafter rotatable to move the substrate into a position from which the substrate may be removed from contact with the drum.

In this last mentioned construction preferably the drum is rotatable to bring one or more aperture into a position below the source so that particulate material from the source falls under gravity through the aperture onto the sticky surface.

In this last mentioned construction preferably the drum is thereafter rotatable to move the aperture(s) away from a position adjacent to the source such that excess particulate material falls away from the substrate back into the source.

In this last mentioned construction the apparatus is suitably provided with a tapper as described above to tap the drum adjacent to the substrate when the aperture is in the position such that excess particulate material can fall away therefrom.

In the apparatus of the invention the further processing means may comprise means to isolate units of the substrate.

For example when the substrate comprises a mass of a sticky substrate deposited upon a release carrier from which it can subsequently be peeled, such means may comprise means to peel the mass together with the particulate material stuck thereon from the release carrier.

For example such means may comprise means to subdivide the substrate. In the case of a sheet-form substrate such subdividing means may comprise cutting means to cut the substrate into units each comprising a desired amount of the particulate material such as a drug substance, e.g. one or more unit dose. Such cutting means may comprise knives or a laser cutter as described above.

The further processing means may also comprise compacting means to compact the substrate.

For example such means may be adapted to compact a sheet-form substrate, e.g. in the form of an elongate strip. Such means may comprise means to roll the substrate into a cylinder, to fold the substrate, or to stack isolated units of the substrate.

Further processing means may also comprise means to enclose or encapsulate a compacted sheet-form substrate in a suitable carrier such as a compacted tablet or capsule. Methods of doing so are well known in the art. Such a compacted tablet or capsule may comprise a drug delivery device of a shape and size suitable to administer the device to the human or animal body, typically the shape and size of a conventional pharmaceutical tablet or capsule or suppository etc.

The apparatus of the invention may also comprise means to measure the amount of particulate material which has become stuck onto the sticky surface.

The invention will now be described by way of example only with reference to the accompanying drawings.

Laboratory Example.

Figure 1:
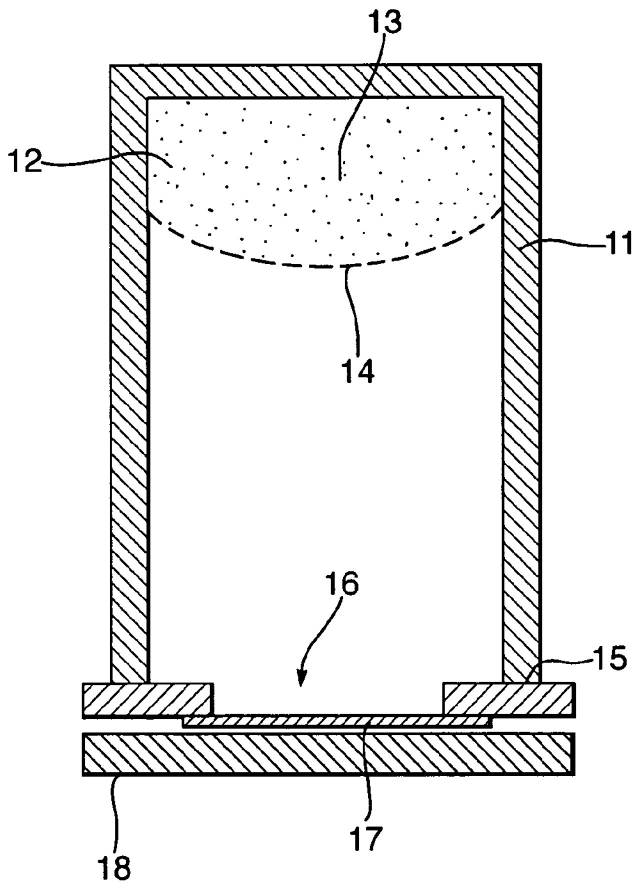
FIG. 1 shows a laboratory form of an apparatus of the invention.

Referring to FIG. 1 this shows a simple form of the apparatus of the invention for performing the process of the invention and for producing a drug delivery device of the invention.

The device of FIG. 1 comprises a source 10 (overall) of a particulate drug substance. The source 10 comprises a cylindrical cap body 11 made of a suitable material e.g. a plastics material. In the upper (in the orientation as shown) part of the body 11 is a compartment 12 containing particulate drug substance 13. The lower (as shown) surface of this compartment 12 is defined by a sieve 14, convex curved bulging toward the lower pat of the cap body 11. The mesh size of sieve 14 is 0.5-0.8 mm. The lower end of body 11 is closed by mask 15, made of stainless steel, ca. 0.5 mm thick. A circular aperture 16 ca. 5 cm in diameter, passes completely through mask 15, the aperture 16 being smaller than the diameter of the sieve 14. Attached to the lower surface of mask 15 is a substrate 17. Substrate 17 is supported by a back plate 18, made of stainless steel material plate.

In experiments various particulate substances were used. These included clumping lactose, free running lactose, and micronised lactose. Also used were a range of drug substances including the drug substance Lamictal (GlaxoSmithKline product).

Substrate 17 comprises a commercially available adhesive tape having an adhesive-coated upper surface by means of which substrate 17 was stuck to the lower surface of mask 15 so that its upper (as shown) sticky surface was exposed to the interior of the body 11 through the mask 15. Substrate 17 was supported by a support 18, comprising stainless steel material plate. An area of the sticky adhesive-coated upper surface of the substrate 17 is thereby exposed through the aperture of the mask 15 and this area is consequently isolated from other areas of the sticky surface.

Various adhesive tapes were used as the substrate 17. These tapes included so-called parcel tape, low tack paper and plastic masking tape, fabric backed high tack duct tape, sticky-backed plastic sheet, aluminium sheet tape, insulation tape, paper sticky labels and so plastic so-called Post-It™ note labels. These tapes are of course unsuitable for use as a drug delivery device but were used to confirm the feasibility of the process and to investigate the consistency and precision of the process.

In a typical experiment the compartment 12 was loaded with 3-10 g of particulate substance, the source 10 was oriented upside down to the orientation shown in FIG. 1, and the source 10 was tapped vertically so that the particulate substance was moved through the sieve mesh into compartment 12. Separately the tape substrate 17 was cut to a suitable length, weighed, then stuck to the underside of mask 15 as shown around the rim of the aperture 16. With the cap body inverted relative to the orientation in FIG. 1 the mask 15 was attached to the upper (in this inverted orientation) rim of the cap body 11. The cap body 11 was then re-inverted into the position shown in FIG. 1, and the cap body 11 tapped ten times so that particulate substance 13 fell through sieve 14 onto the region of the sticky surface of the tape substrate 17 exposed through aperture 16 until all of this region of the sticky surface was covered with the particulate substance. Hand tapping of the cap body 11 along the direction of the cylindrical axis of the cap body 11 was found to optimise passage of the particulate substance through the sieve 14. The cap body was then re-inverted so that mask 15 was uppermost and the body 11 was tapped vertically ten times again to remove excess particulate substance from the tape substrate 17. The tape substrate 17 was then peeled from the mask 15, folded to prevent loss of particulate substance, and weighed to determine the weight of particulate drug substance which had become stuck to the sticky surface of the substrate.

The table below illustrates some results obtained using various particulate materials.

| Particulate material | Characteristic | Dispense method | Deposition density mg/cm$^2$ |
|---|---|---|---|
| Clumping lactose | Dry, clumping | Sieved | 1.6 |
| Free running lactose | Free running | Sieved | 5.4 |
| Micronised lactose | Sticky, clumping | Not sieved | 0.4 |
| Micronised lactose | Sticky, clumping | Fine sieve | 0.1 |

Figure 2:
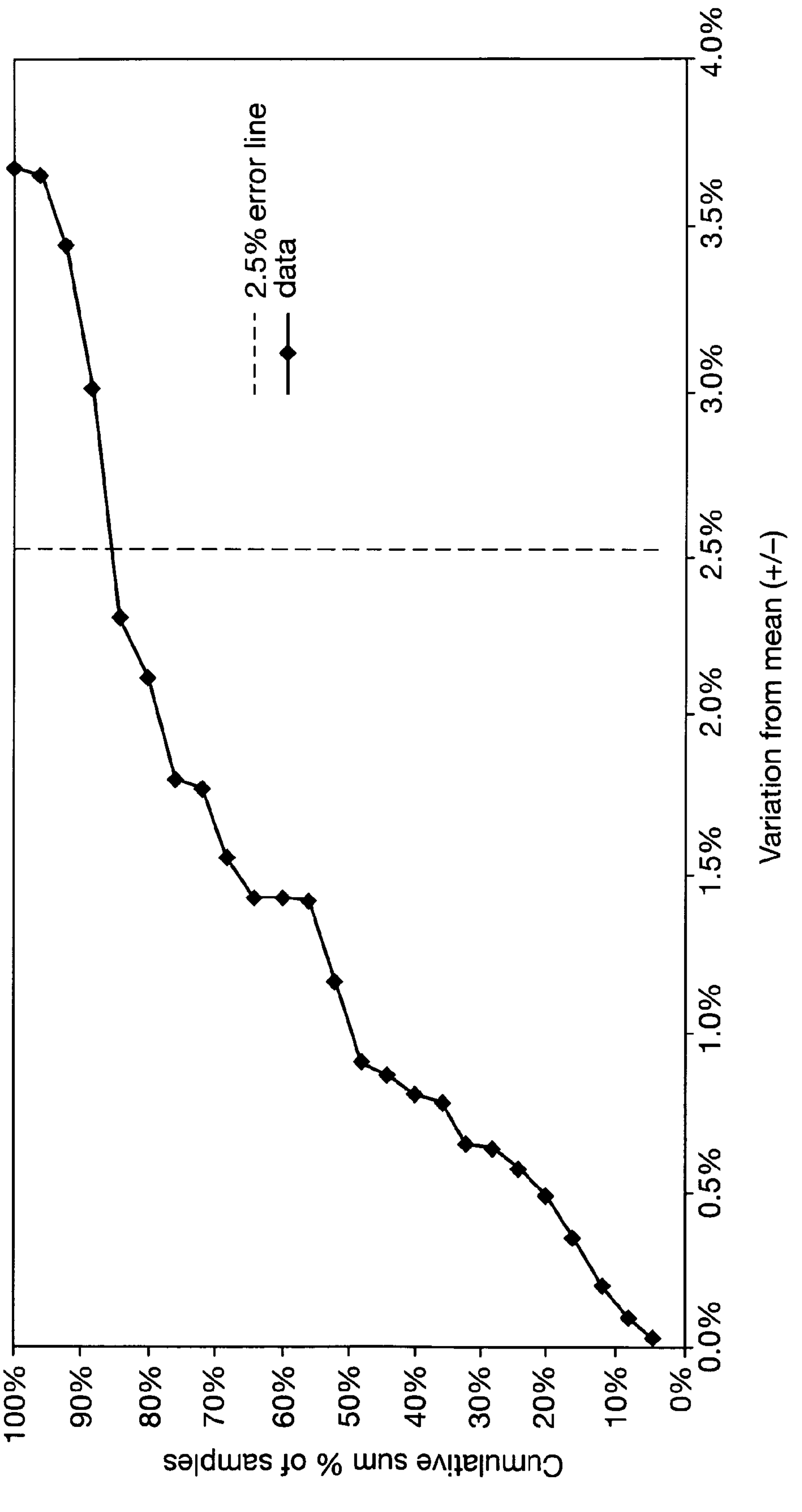
FIG. 2 shows graphically the consistency of deposition weight.

A noticeable feature of the process is the precision and consistency of the weight of particulate substance which becomes stuck to the sticky surface. This is shown in graphical form in FIG. 2 which shows the cumulative variation from mean of the weight of a drug substance SB 659032 supplied by GlaxoSmithKline plc. This substance had a d50 of 25.2 microns (size distribution in microns was d10=5.4, d50=25.2, d90=73.5, span=2.7) sticking onto the sticky tape substrate. In this experiment a standard duct tape was used. This graph shows that some 85% of deposition samples produced by these experiments fell within +/−2.5% of the mean weight (the mean weight over the 25 samples was 10.5 mg). Such a consistency would be suitable for many pharmaceutical drug delivery devices.

It was also noted that particulate substances in the form of a clumping powder showed uniform distribution, whereas free running powder tended to show discrete powder lumps, and high frequency vibration of the mask also tended to result in clumping.

Figure 3:
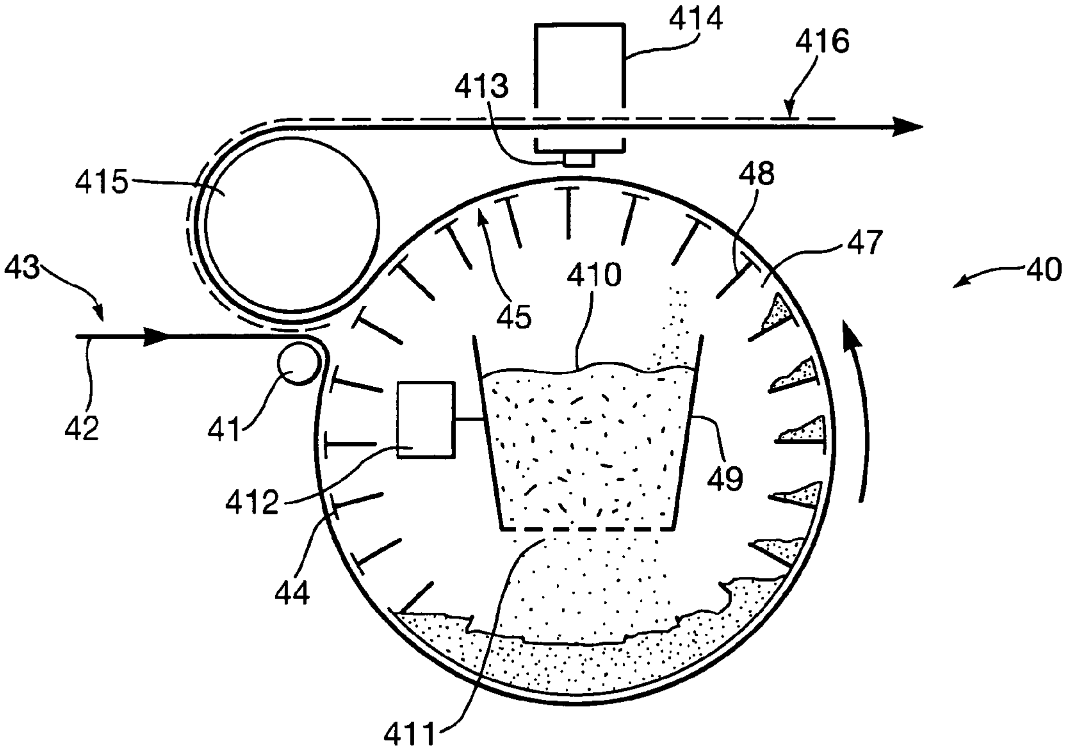
FIG. 3 shows a schematic diagram of a commercial form of the apparatus of the invention.

FIG. 3 shows a schematic diagram of a suitable apparatus 40 overall, for performing the process of the invention. The apparatus 40 comprises a feed roller 41 by means of which a substrate 42 may be fed into the apparatus from an external supply (not shown). The substrate 42 comprises an elongate strip-form flexible material, with an upper (as shown) sticky surface 43 thereon.

The roller 41 feeds the substrate 42 toward a rotatable cylindrical hollow drum 44 such that the substrate 42 becomes wound around drum 44 and stuck to the outer surface of the drum 44 by means of the sticky surface 43 of the substrate 42 in sticky contact with the outer surface of drum 44. Roller 41 can also press the substrate 42 against the drum. Further rollers (not shown) may be used to press the substrate against drum 44 to enhance sticky contact between the substrate and the drum. Tension may also be applied to the substrate 42 by appropriate means, which may be generally conventional, to thereby hold the substrate 42 against drum 44.

Figure 4:
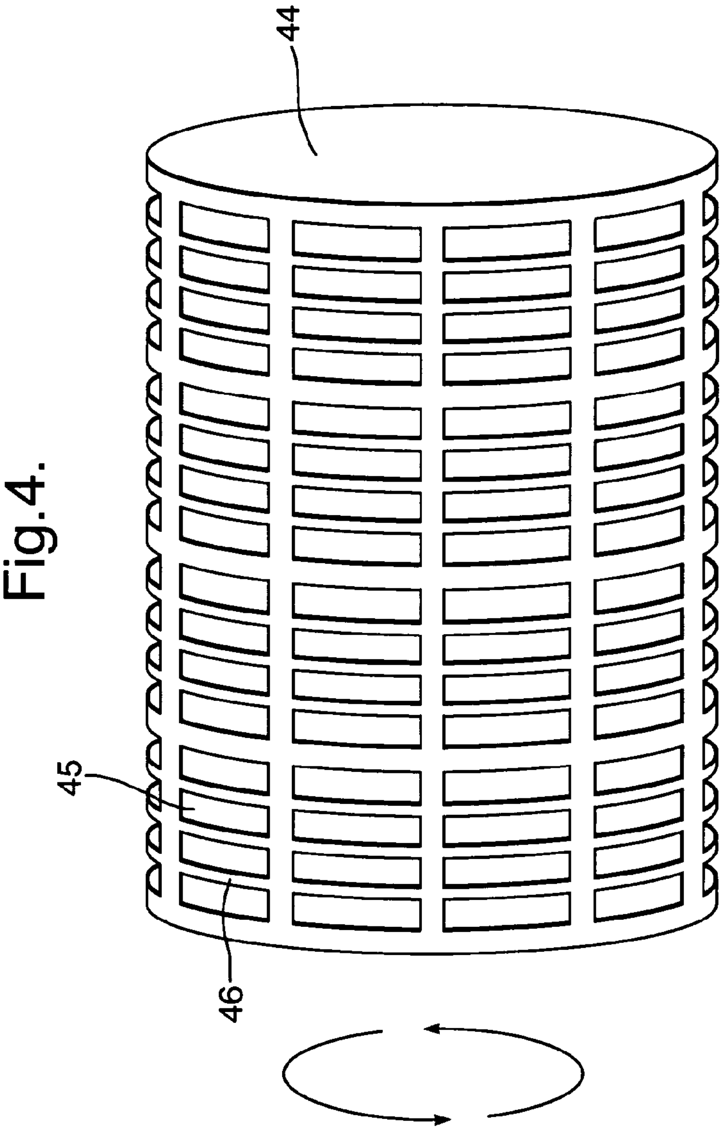
FIG. 4 shows a drum of the apparatus of FIG. 3.

FIG. 4 shows a schematic perspective view of drum 44. The drum 44 comprises plural apertures 45 through the wall of the drum 44, the residual wall of the drum between the apertures 45 being retained as impermeable webs 46 between the apertures and to which the sticky surface 43 of substrate 42 sticks. The apertures 45 may be bridged by thin cross-links (not shown) to reinforce the structure of the drum 44 and to support the substrate 42. Internally the inner surface of the wall of the drum 44 is divided into circumferentially disposed cells 47 by means of radial partition walls 48 each extending radially inwardly from a web 45, although the drum 44 need not be so divided. Each partition wall 47 divides an aperture 45 from its circumferentially adjacent aperture 44. The sticky surface 43 of substrate 42 is exposed to the interior of the drum 44 through the apertures 45. The apertures 45 may be simple openings through the wall of the drum 44, alternatively apertures 45 may be provided as inserts comprising one or more aperture 45 in each module, and which can be attached to the drum 44. Such inserts may for example provide improved aperture accuracy, or facilitate changing the amount of particulate material 410 stuck to the sticky surface. An area of the sticky upper surface 43 of the substrate 42 is thereby exposed through the aperture 45 of the drum 44 and this exposed area is consequently isolated from other areas of the sticky surface 43.

Within the cylindrical drum 44 there is a hopper 49 of the particulate material, e.g. a drug substance 410 having a lower dispensing opening closed with a sieve 411, through which particulate material 410 may pass. Hopper 49 may also be provided with means 412 to apply vibration to the hopper 49, or such means may for example comprise a stirrer, ultrasonic vibrator etc. acting directly on the material 410 in the hopper 49. Particulate material 410 passing through sieve 411 falls into the cells 47 passing beneath sieve 411 as the rotation of drum 44 carries the cells beneath the sieve 411. Particulate material 410 in the cells 47 becomes stuck to the areas of sticky surface 43 of the substrate 42 exposed to the interior of the drum 44. The hopper 49 may be agitated to encourage even distribution of the particulate material 410 over the sticky surface 43, i.e. to keep all of the particles of the material 410 moving, and to encourage a generally downward flow of the particulate material 410.

The hopper 49 may be continuously filled by continuous filling means (not shown) of conventional construction. Modular hoppers 49 may be provided each containing a different particulate material 410 to suit corresponding applications. Alternative types of source of particulate material than a hopper could be used, such as a powder blower to direct a stream or cloud of particles of the particulate material 410 toward the apertures 45.

As drum 44 continues to rotate the cells 47 move to a position above the upper open end of the hopper 49 and excess particulate material 410 which is not stuck to the sticky surface 43 falls from the cells 47 back into the hopper 49.

To encourage the excess particulate material 410 to fall from the substrate 42, a tapper 413 is provided adjacent to the highest point of drum 44. Tapper 413 comprises a reciprocally movable piston which is reciprocally moved by solenoid 414 (shown partly obscured by substrate 42) and is positioned to tap the upper surface of drum 44 adjacent to the substrate 42 to thereby knock any non-stuck excess material 410 off the substrate 42 and back into hopper 49.

Additional or alternative means to remove excess particulate material 410 may be used such as air streams (e.g. air knives), agitation or vibration e.g. sonic vibration, brushing e.g. on the opposite surface of the substrate 42 to that 43 which is sticky.

Continued rotation of the drum 44 moves the substrate 42 stuck thereto into a position from which the substrate 42 is removed from sticky contact with the drum 44 by means of the generally conventional take-off roller 415. Thereafter the substrate 42, with patches of the particulate substance 410 stuck to its sticky surface at areas 416 corresponding to apertures 45 is led away to a further processing means (not shown).

Figure 5:
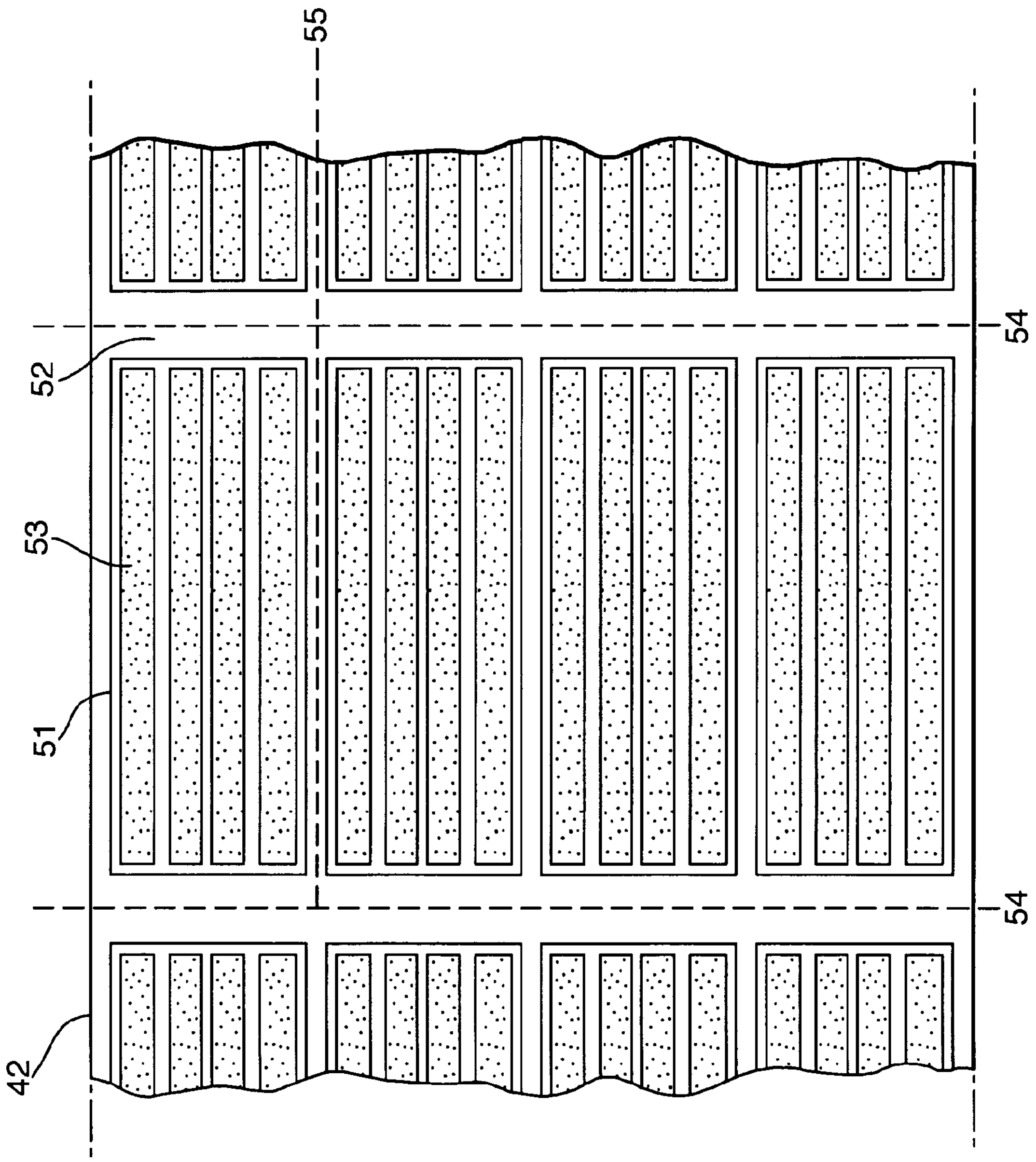
FIG. 5 shows substrates produced using the apparatus of FIG. 3.

FIG. 5 shows a typical layout in plan view looking down onto sticky surface 43 of deposited patches of particulate substance 411 on the surface of the substrate 42 as produced by an apparatus of FIG. 3 using a drum of FIG. 4. Patches 51 of sticky substance have been applied to the surface of the sheet-form substrate base. The patches 51 are of a shape corresponding to the shape of an array of four apertures 45 in the wall of the drum 44 with regions 52 of surface of the substrate base 42 without sticky substance thereon. Patches 53 of particulate material corresponding to the shape and position of the apertures 45 are deposited on the patches 51 of sticky substance. The substrate 42 may be cut respectively longitudinally and widthways at lines 54, 55 in the regions 53 between the patches 51 of sticky substance to thereby form units of the substrate 42 having a single patch 51 of the sticky substance. Such units may be further processed in a generally conventional manner by being rolled and cut into four small cylinders or folded into small packages enclosing the patch 51 within them. Such small cylinders or packages can then be further encapsulated or otherwise enclosed within a protective and/or aesthetically attractive outer cover to provide a drug delivery device suitable for use.

Figure 6:
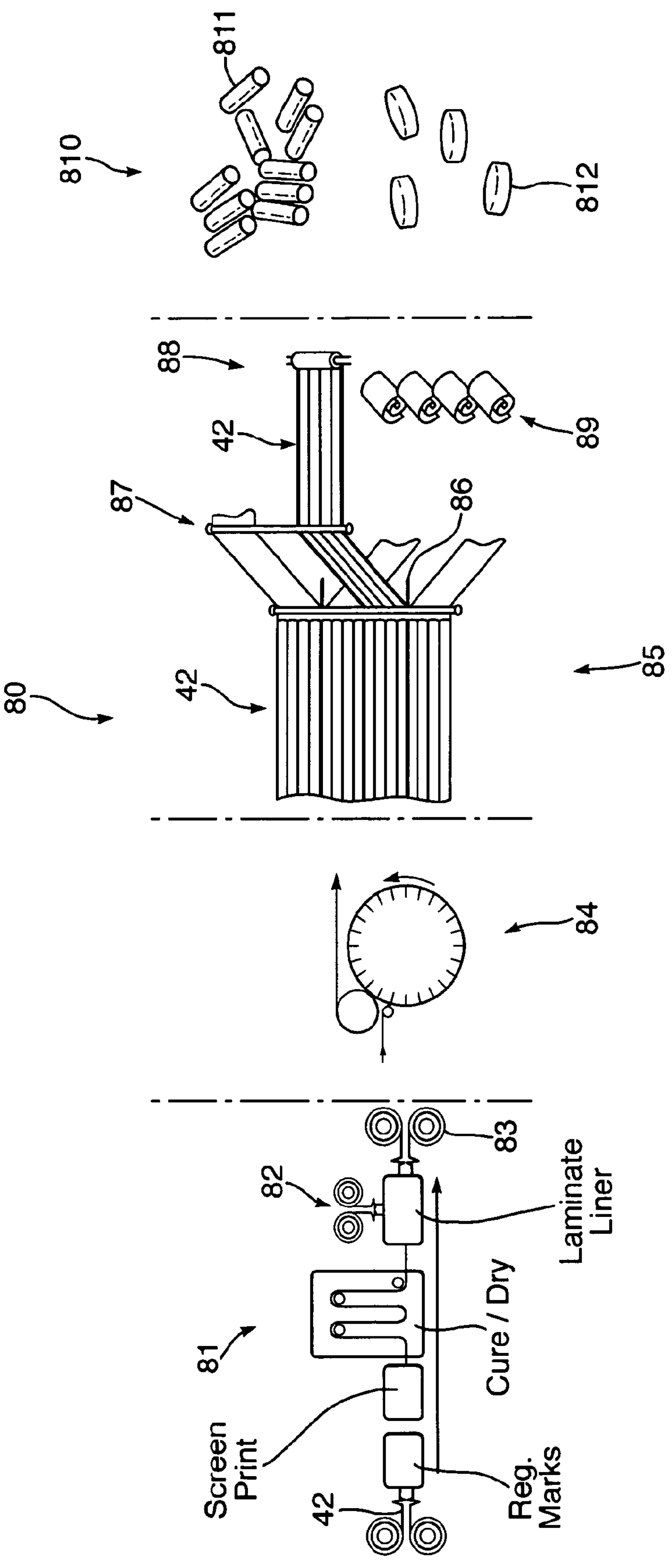
FIG. 6 shows schematically an overall manufacturing system.

FIG. 6 shows schematically how an overall manufacturing system 80 based upon an apparatus might be set up. At 81 is shown a generally conventional printing system wherein sticky material is applied to the surface of an elongate strip-form substrate 42, and a protective liner 82 applied. The substrate 42 with its protective liner 82 may then be stored on rolls 83 prior to use.

At 84 is schematically shown an apparatus 40 as shown in FIG. 4. The apparatus 40 is fed with substrate 42 from which the protective liner 82 has been removed to expose the sticky surface 43. At 85 is shown how the substrate 42 proceeding from the apparatus 40, and with particulate material 410 deposited thereon, is slit longitudinally, e.g. along lines 55 as seen in FIG. 5, by knives 86, then substrate 42 is guided by roller 87 toward a generally conventional rolling means at 88, to produce small cylindrical units 89 as shown in FIG. 5. The substrate 42 can be cut widthways, e.g. along lines 54 as seen in FIG. 5 to isolate suitable areas of the substrate 42 in the units 89. As illustrated in FIG. 8 the units 89 have four (there may be more or less) stripes of sticky surface in line across its length, each stripe in turn each having four (there may be more or less) stripe-shaped patches of particulate drug substance stuck thereon.

The units 89 each enclose the four stripe-shaped patches 53 of particulate drug substance therein. These cylinders 89 may themselves be further processed by cutting across their cylindrical length into shorter cylinders each enclosing one or more stripe-shaped patch 53 of particulate drug substance therein.

At 810 cylinders 89, or cylinders 89 cut as last-described, are shown encapsulated in capsules 811 or compacted within compacted tablets or caplets 812. The overall system 80 should be operated according to GMP and under environmental conditions appropriate to the drug delivery device.

A particular drug delivery device application will depend inter alia upon the substance and the weight of the substance which it is desired to incorporate in the drug delivery device. For example, based upon the deposition densities weight:unit area discussed above multiple doses of 5 mg of a particulate drug substance may be incorporated on a substrate 42 as shown in FIG. 5 having a width of ca. 180 mm. Such a substrate 42 may have deposited on its surface four patches 51 abreast of sticky material each of a width ca. 44 mm. Each such patch 51 may have four patches 53 thereon of particulate substance each ca. 42 mm long (in the direction of movement of the strip through the apparatus of FIG. 3) and 8 mm wide.

Correspondingly, doses of 20 mg of a particulate drug substance may be incorporated on a substrate 42 as shown in FIG. 5 a width of ca. 180 mm. Such a substrate 42 may have deposited on its surface four patches 51 of sticky material each of a width ca. 44 mm. Each such patch 51 may have four patches 53 thereon of particulate substance each ca. 170 mm long and 8 mm wide.

Correspondingly, doses of 100 mg of a particulate drug substance may be incorporated on a substrate 42 as shown in FIG. 5 having a width of ca. 340 mm. Such a substrate 42 may have deposited on its surface four patches 51 abreast of sticky material each of a width ca. 84 mm. Each such patch 51 may have four patches 53 thereon of particulate substance each ca. 370 mm long and 18 mm wide.

Dimensions of the substrate 42, drum 44 and other parts of the apparatus may be determined experimentally for particular drug delivery devices. For example for production of drug delivery devices comprising 5 mg of particulate drug substance a drum 65 mm in diameter and 180 mm wide may be suitable, depositing particulate drug substance on four patches 51 of sticky material per rotation of the drum 44. Proportionally sized drums may be used for deposition of other amounts of particulate drug substance, for example:

| Wt. drug substance | Drum diam. mm | Drum width mm | Patches/rotation. |
|---|---|---|---|
| 5 mg | 65 | 180 | 4 |
| 5 mg | 130 | 180 | 8 |
| 20 mg | 65 | 180 | 1 |
| 20 mg | 130 | 180 | 2 |
| 100 mg | 130 | 340 | 1 |

Estimations of the performance of the apparatus of the invention operated as above suggest that with a drum 44 operating at 30 rpm such an apparatus can produce 4000 drug delivery devices per minute comprising 5 mg of drug substance, or 1000 drug delivery devices comprising 20 mg of drug substance, or 500 drug delivery devices comprising 100 mg of drug substance with a consistency in the weight of substance deposited of ca. 4%.

It is also estimated that units of substrate 42 prepared as above may be further processed by rolling into small cylinders having dimensions convenient for use as a drug delivery device. For example it is estimated that a device comprising 5 mg of drug substance could be rolled into cylinders 10 mm long and 2.3 mm diameter, comprising 20 mg of drug substance into cylinders 10 mm long and 4.6 mm diameter, or comprising 100 mg of drug substance into cylinders 20 mm long and 6.9 mm diameter.

Figure 7A:
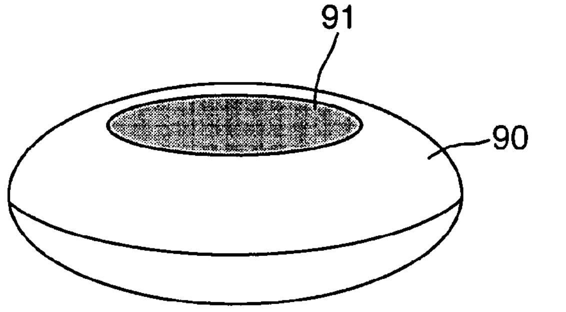
FIG. 7 shows alternative types of drug delivery device according to the invention.
Figure 7B:
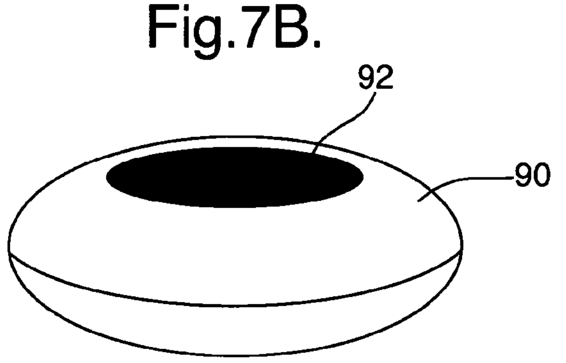
Figure 7C:
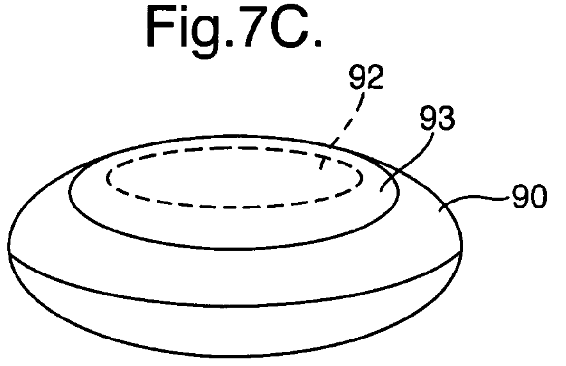

Referring to FIG. 7, FIG. 7A shows a substrate base 90 comprising a rigid solid article, being a compacted tablet, made of typical inert materials as used in the pharmaceutical industry, e.g. excipients such as filler, lubricant, disintegrating agent etc. A patch of sticky substance 91 has been applied to the surface of the base 90. FIG. 7B shows a particulate drug substance 92 has been brought into contact with the sticky substance 91 and has become stuck thereto. Excess particulate drug substance 92 has been removed from the sticky surface 91, and as shown in FIG. 7C a cover layer 93 has been applied over the particulate material 91.

Figure 8A:
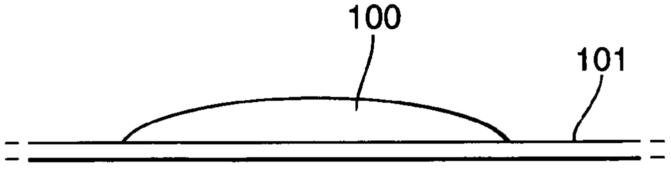
FIG. 8 shows an alternative type of drug delivery device according to the invention.
Figure 8B:
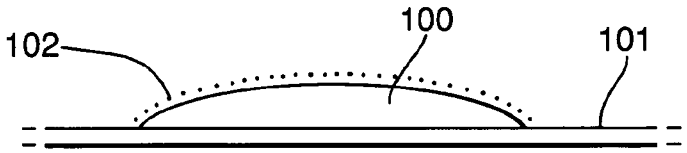
Figure 8C:
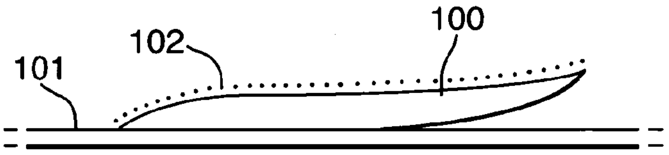
Figure 8D:
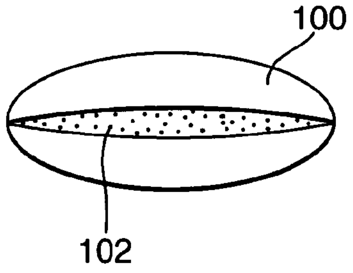

FIG. 8, in FIG. 8A shows a mass 100 of a sticky substrate deposited upon the surface of a release carrier 101 in the form of a sheet-form flexible material, for example having a silicone coated surface. In FIG. 8B a particulate material 102 has been brought into contact with the sticky substance 100 and has been stuck thereto. In FIG. 8C excess particulate material 102 has been removed from the sticky substance 100, and the mass 100 with its particulate material 102 stuck thereto is being peeled off from the release carrier 101. For example this may be achieved by curving the carrier 101 so that the side facing the mass 100 becomes convex. In FIG. 8D the mass 100 has been folded to enclose the particulate material 102.

Figure 9:
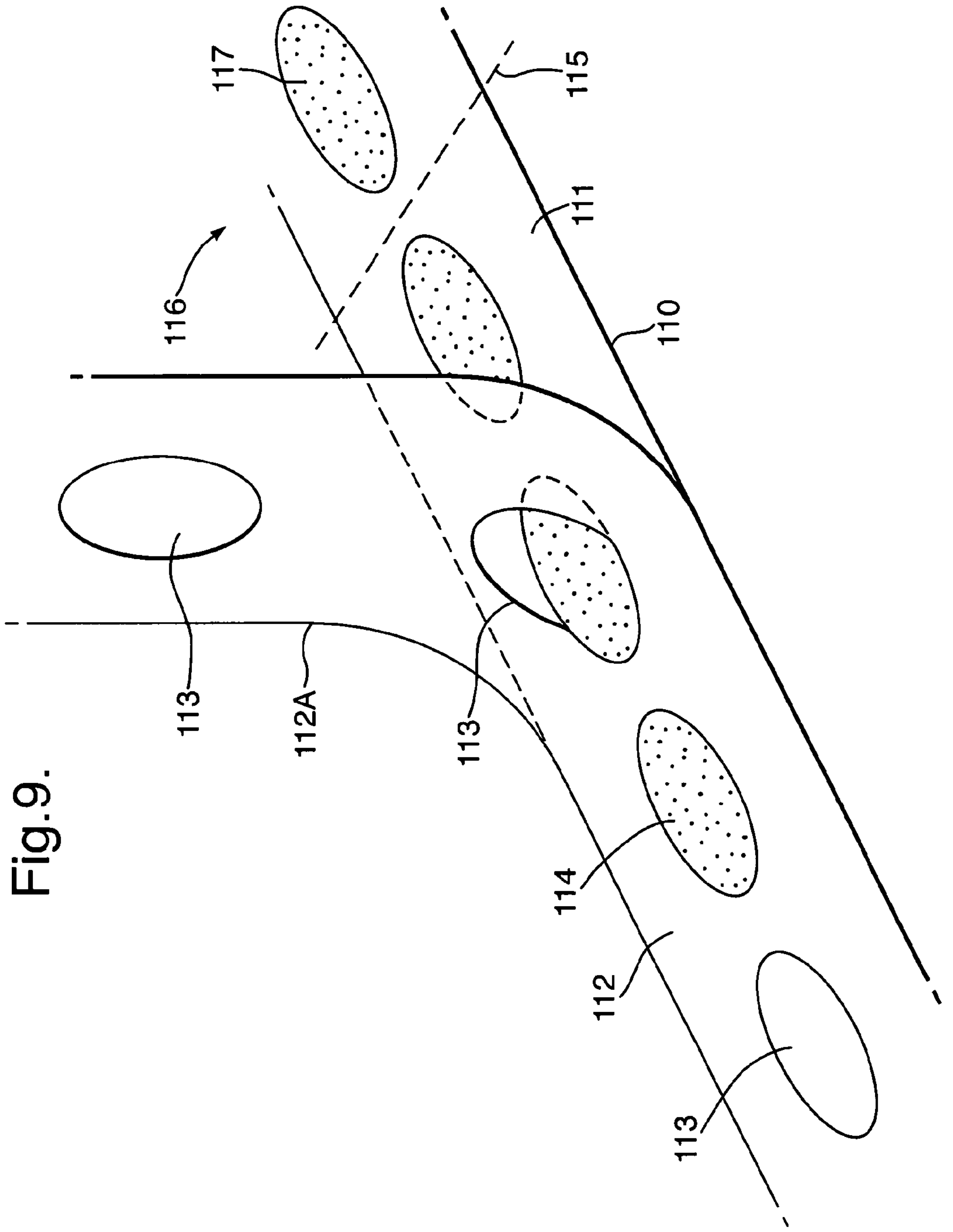
FIG. 9 shows an alternative type of drug delivery device according to the invention.

FIG. 9 shows a substrate 110 in the form of an elongate strip of flexible sheet-form substrate base with a sticky substance on its surface 111, with a film-form mask 112 stuck to the surface 111 by means of the sticky substance. The film-form mask 112 has apertures 113 therethrough exposing regions of the sticky substance. A particulate material 114 has been brought into contact with the sticky substance 111 through the apertures 113 and has become stuck to the sticky substance 111. Excess particulate material is removed e.g. by gently blown air. Then the film-form mask at 112A is peeled from the sticky substrate 110 to leave patches of particulate material 114 in patches on the surface 111. The substrate 110 may be cut across its length at lines 115 to form isolated units 116 of the substrate 110 comprising a defined area 117 of the sticky surface 111 having the particulate material 114 stuck thereto. The units 116 may be folded or rolled as above to provide compacted forms of the substrate 110 e.g. for use as a delivery device for a particulate drug substance.

Figure 10:
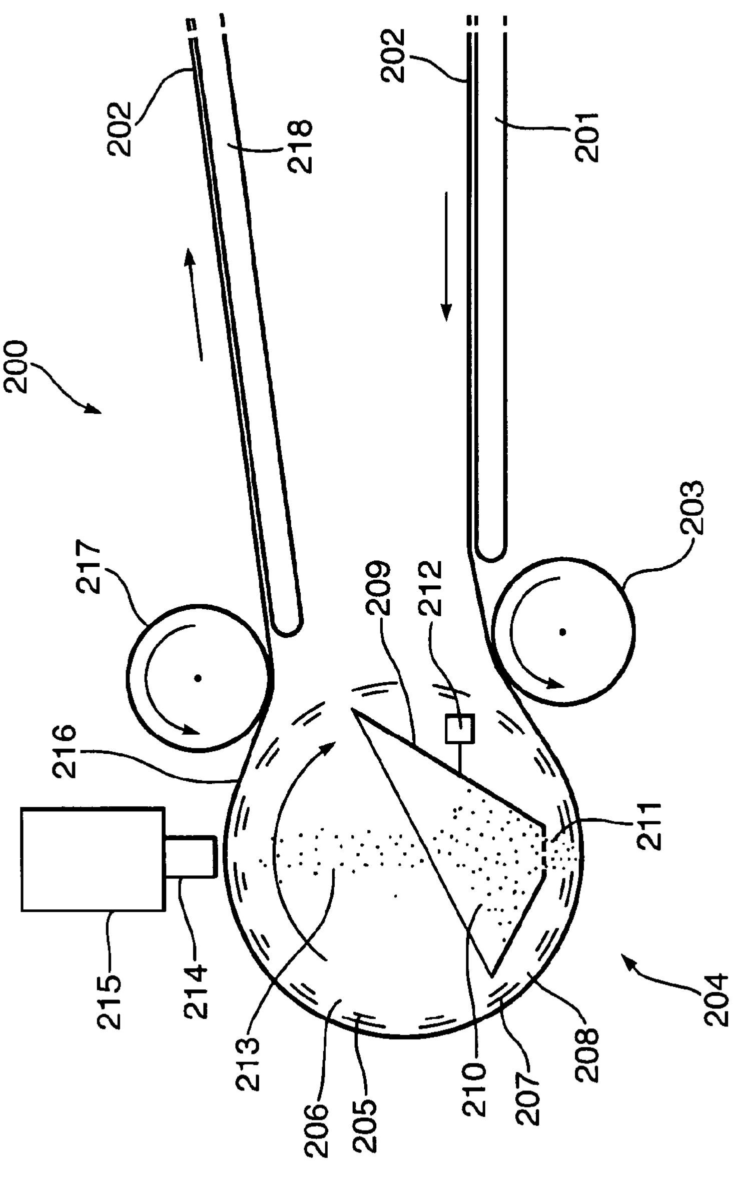
FIG. 10 shows a schematic diagram of an alternative commercial form of the apparatus of the invention.

Referring to FIG. 10, this shows overall 200 another construction of an apparatus of the invention suitable for commercial operation. The apparatus 200 comprises a guide 201 along which a substrate 202 is fed into the apparatus 200 from an external supply (not shown). The substrate 202 comprises an elongate strip-form flexible material, with an upper (as shown) sticky surface thereon analogous to that of the apparatus of FIG. 3.

The guide 201 leads the substrate 202 to guide roller 203 which in turn guides the substrate 202 towards rotatable cylindrical hollow drum 204, which is rotated by a motor (not shown). The rotation of drum 204 drives the substrate 204 through the apparatus. Drum 204 is of two-part construction comprising two concentric drums both made of stainless steel, being an inner drum 205 provided with relatively large apertures 206 through its wall, radially over which is located an outer drum 207 provided with relatively smaller apertures 208 through its wall, the outer drum 207 being supported by the inner drum 205 (though a gap is shown between inner drum 205 and outer drum 207 in practice they are in contact). These relatively smaller apertures 208 determine the area of the sticky surface of the substrate 202 exposed to the particulate material through them. The outer drum 207 is removable from the inner drum 205 and can be replaced upon it, or can be replaced by an alternative outer drum, not shown, with apertures 208 of a different size, position and/or shape to those 208 on the drum 207. This inner drum 205 and outer drum 207 construction facilitates removal and cleaning of the outer apertures 208.

As is seen in FIG. 10 the substrate 202 becomes wound around drum 204, specifically around the outer drum 207, and becomes stuck by means of its sticky surface to the outer surface of the drum 204. Roller 203 can also be configured to press the substrate 202 against the drum 204 to enhance sticky contact between the substrate 202 and the drum 204. Tension may also be applied to the substrate 202 by appropriate means, which may be generally conventional, to thereby hold the substrate 202 against drum 204.

Within the cylindrical drum 204 there is a hopper 209 of the particulate material 210, e.g. a drug substance. The hopper 209 has a lower dispensing opening closed with a sieve 211 through which particulate material 210 may pass. Hopper 209 is also provided with a mechanical vibrator 212 to apply vibration to the hopper 209.

Particulate material 210 passing through sieve 211 falls through apertures 207, 208, comes into contact with the sticky surface of substrate 202 wrapped around drum 204 and becomes stuck to the areas of sticky surface 43 of the substrate 202 exposed to the interior of the drum 204 through the apertures 207,208. An area of the sticky upper surface of the substrate 202 is thereby exposed through the apertures 207, 208 of the drum 204 and this exposed area is consequently isolated from other areas of the sticky surface of the substrate 202.

The hopper 209 may be continuously filled by continuous filling means (not shown) of conventional construction. Modular hoppers 209 may be provided each containing a different particulate material 210 to suit corresponding applications. Alternative types of source of particulate material 210 than a hopper 209 could be used, such as a powder blower to direct a stream or cloud of particles of the particulate material 210 toward the apertures 207,208.

Figure 10A:
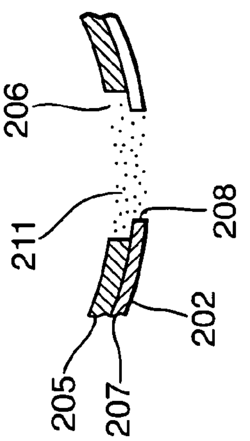

As drum 204 continues to rotate the apertures 207,208 move to a position above the upper open end of the hopper 209 and excess particulate substance 213 which is not stuck to the sticky surface 43 falls from the surface of substrate 202 back into the hopper 209. A further advantage of this inner drum 205 and outer drum 207 construction is seen from FIG. 10A which shows schematically an enlarged section through the inner and outer drums 205,208 and a substrate 202 wound upon it. It is seen that the smaller dimensions of the outer aperture 208 relative to the inner aperture 206 results in a stepped cavity in which particulate material 210 can sit, with a reduced tendency of the particulate material 210 to tumble around inside the drum 204.

To encourage the excess particulate material 213 to fall from the substrate 202, a tapper 214 is provided adjacent to the highest point of drum 204. Tapper 214 comprises a reciprocally movable piston which is reciprocally moved by solenoid 215 and is positioned to tap the upper surface of drum 204 adjacent to the substrate 202 to thereby knock any non-stuck excess material 213 off the substrate. Additional or alternative means to remove excess particulate material 213 may be used such as air streams (e.g. air knives), other forms of agitation or vibration e.g. sonic vibration, or brushing.

Continued rotation of the drum 204 moves the substrate 202 stuck thereto into a position 216 from which the substrate 202 is removed from sticky contact with the drum 204 and is guided by means of the generally conventional take-off roller 217 toward off-loading guide 218.

Thereafter the substrate 202, with patches of the particulate substance stuck to its sticky surface 43, is led away to a further processing means (not shown) analogous as above.

A machine as shown in FIG. 10 was constructed with the following operating characteristics.

| | |
|---|---|
| Outer diameter of drum 207: | 100 mm |
| Number of apertures 206, 208: | 8 in each drum |
| Rotation speed of drum 204: | 8 rpm |
| Circular diameter of apertures 208: | 20 mm |
| Tapper rate: | One tap per second |

In this machine the tapper 214 had a mass of 32 g and was driven downwards by a spring with a force of 1.6 N over a drop of 16 mm to contact the drum 204. The tapper was held raised away from drum 204 when the solenoid 215 was powered and allowed to drop when the power was switched off.

Figure 11:
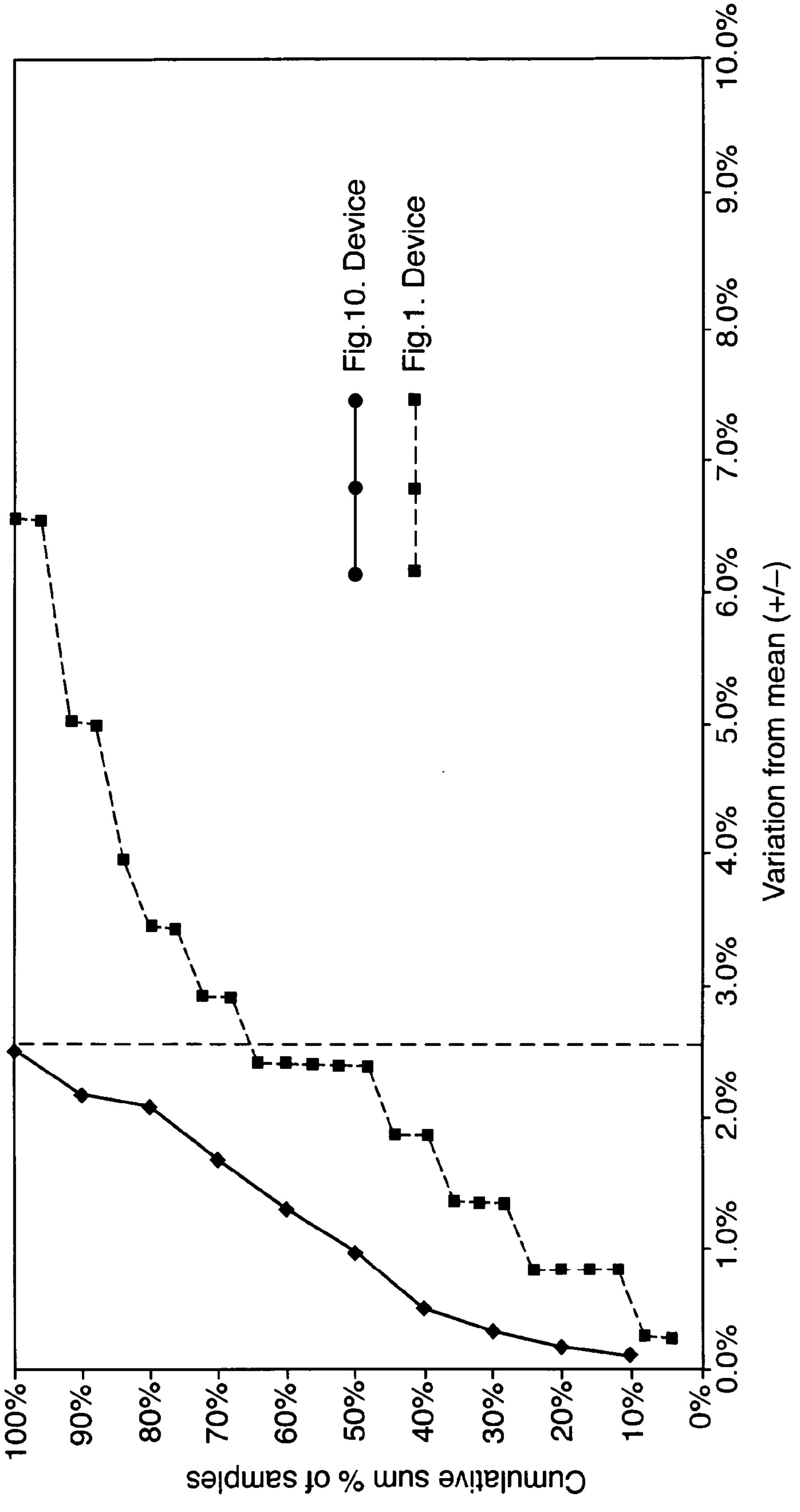
FIG. 11 shows a comparison of variation of dose using the devices of FIGS. 1 and 10.

Referring to FIG. 11 this shows the variation in the weight of a particulate material, lactose powder, using a device as shown in FIG. 1 and as shown in FIG. 10. In the experiment plural circles of duct tape were cut out and used as the substrate 18 shown in FIG. 1. These circles were weighed prior to dosing with the lactose powder as described above, then weighed again after powder dosing. Plural similar circles of duct tape were cut out, weighed, each successively placed over the same aperture 207 of a drum 204 as shown in FIG. 10, with the aperture 207 initially distant from the hopper 209, then the drum 204 was put through one revolution with the vibrating hopper 209 and tapper 214 both activated. When the circle of duct tape had rotated to a position distant from the tapper 214 it was removed from the drum 204 and weighed. The results shown in FIG. 11 show less variation from mean using the device of FIG. 10 than with the device of FIG. 1.

Figure 12:
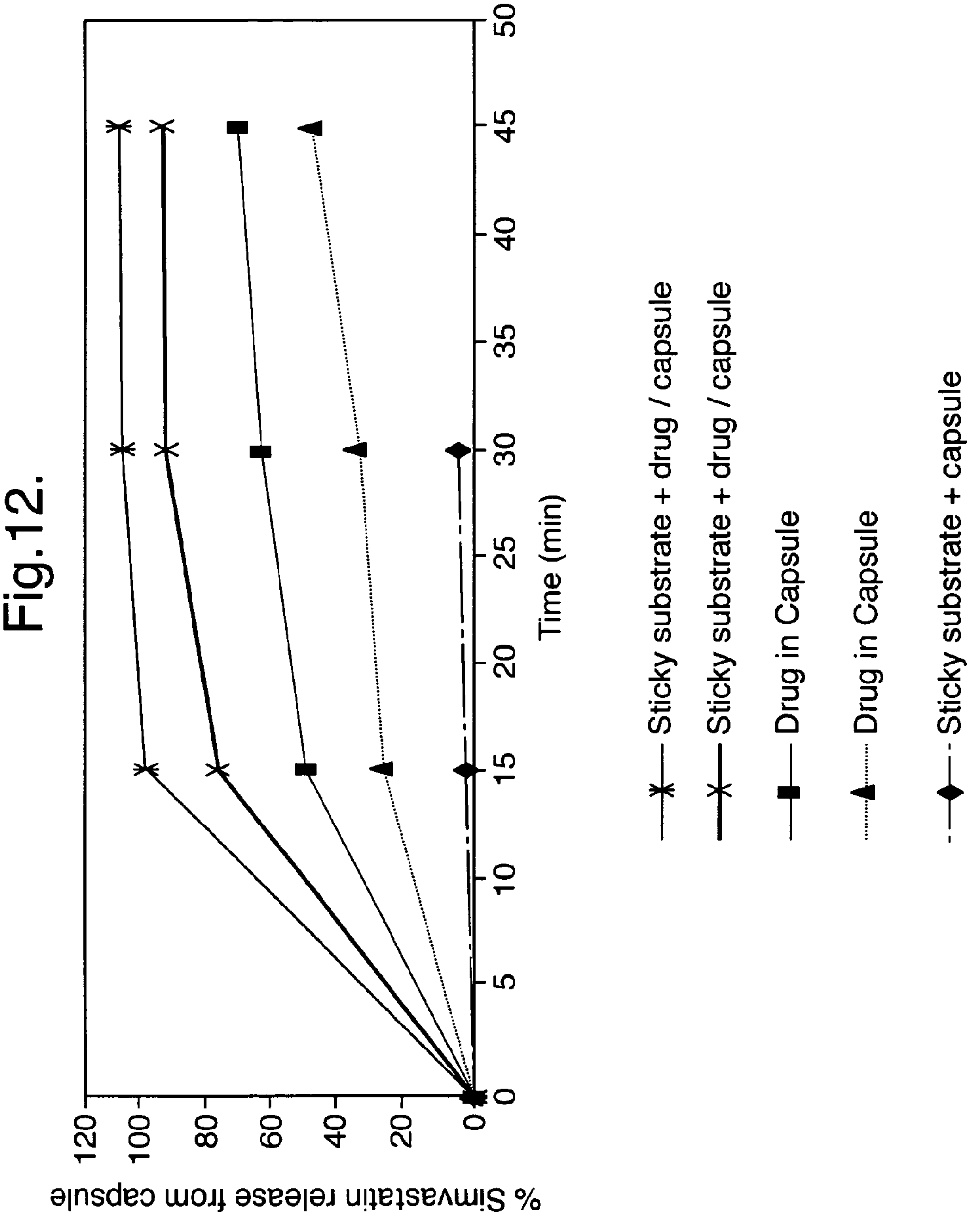
FIG. 12 shows graphically a comparative dissolution experiment using a dosage form of this invention and other dosage forms.

Referring to FIG. 12 this shows results of dissolution experiments in which a drug compound (Simvastatin, supplied by GlaxoSmithKline) was deposited on a Monosol substrate with a surface having the sticky substance described above (Glycerine 47.5 wt %, powdered gelatine 34.0 wt %, water 14.2 wt % and a black food dye 4.3 wt % for visibility, prepared as described below) thereon, using an apparatus as shown in FIG. 1. The patches of deposited Simvastatin so formed were cut from the bulk of the substrate strip, rolled into small cylinders with the Simvastatin thereby covered by the monosol sheet material. These cylinders were then enclosed in a standard gelatin pharmaceutical capsule, weighted down in a metal cage, and immersed in a dissolution medium. Dissolution of the Simvastatin into the dissolution medium was monitored with time. As a comparison the same weight of free Simvastatin powder was simply encased in a similar capsule, weighted down in the same way in the same medium and dissolution was also monitored. In another comparison an identical sticky substance on an identical substrate was encased in a similar capsule without application of Simvastatin. With the exception of the capsule not containing Simvastatin, in each experiment the same weight, 2 mg, of Simvastatin was either deposited on the substrate or enclosed within the comparison capsule.

The dissolution data shown in FIG. 12 indicate on the vertical scale the percentage of the content released from the capsule. It can be seen that dissolution of the Simvastatin from the capsule containing the Simvastatin deposited on the sticky surface substrate occurred more quickly than from the free powdered Simvastatin. Although this invention is not limited to any technical effect it is believed that the enhanced dissolution from the substrate of the present invention may be due to the increased surface area of the Simvastatin resulting from the avoidance of clumping of the particles.

(NB: Apparent dissolution of more than 100% of the Simvastatin is attributed to a HPLC peak from the substrate or sticky substance appearing in the same position as the Simvastatin in the trace, as can be seen from the data for the capsule containing no Simvastatin.)

The gelatin-glycerin-water sticky substance was made as follows. The following ingredients were used:

| Ingredient | Source | Proportion wt. % | Mass (g) |
|---|---|---|---|
| Powdered beef gelatine | Supercook | 34.0% | 11.0 |
| Glycerine | BP 100% | 47.5% | 15.4 |
| Black food colouring | Supercook | 4.3% | 4.8 |
| Distilled water | Recently boiled, 80° C. | 14.2% | 4.6 |
| Total | | 100% | 32.4 |

The powdered gelatine was added to a glass beaker, glycerine was added until the mix was uniform, then the black food dye was added and mixed until uniform. Then the hot water was added and the whole was mixed. The glass beaker containing the mixture was transferred onto a hot plate which had been preheated to 200° C. The mixture was mixed continuously for 17 minutes, after which the powdered gelatine was dissolved, or the time could be altered to achieve this.

A calendaring machine with an adjustable gap was provided. Two sheets of silicone coated paper were provided, of a width suitable for the roller width, and of a length as required. These sheets were positioned between the two rollers. A quantity of the hot adhesive mixture was transferred onto the paper centrally above the rollers. The rollers were driven to thereby squeeze the soft adhesive mixture flat between the paper sheets. The paper sheets with the flattened layer of adhesive between them was removed from the rollers and placed on a flat marble slab to cool. Once cool, one sheet of the paper was carefully peeled away so as not to disturb the adhesive from the other sheet. Typically layers of the sticky substance 50-100 microns thick could be made in this way.

Discs of this sticky substance could be cut by using a hole cutter with the marble slab under the paper, without cutting through the paper itself. A substrate could be applied to the isolated disc of adhesive so formed and the disc of sticky substance could then be peeled away from the paper attached to the substrate. The adhesive disc attached to the substrate could then be covered with a protective layer e.g. aluminium foil until use as described above.

The invention claimed is:

1. A process for providing a quantity of a drug substance, comprising: providing a substrate in the form of a sheet of flexible material having patches of a coating of a sticky substance on its surface with areas free from the sticky substance located between said patches, bringing drug substance into close proximity with the sticky substance so that a portion of the drug substance becomes stuck to the sticky substance, removing from the substrate excess drug substance which has not become stuck thereto, isolating a unit of the substrate comprising an area of the sticky substance and the portion of the drug substance stuck thereto by dividing the substrate at areas free from the sticky substance located between said patches, then processing the substrate to compact the substrate such that the sticky substance causes areas of the surface of the substrate to stick together to thereby enclose the drug substance within the compacted substrate.

2. A process according to claim 1 in which said processing compacts the unit into a form suitable as a drug substance delivery device.

3. A process according to claim 1 wherein the sticky substance comprises a mixture of glycerine and gelatin in a weight ratio 2.4+/−0.1:3+/−0.1.

4. A process according to claim 1 wherein said substrate comprises hydroxypropyl methyl cellulose.

5. A process according to claim 1 in which the step of isolating a unit comprising a patch of the sticky substance and the portion of the drug substance stuck thereto is carried out by positioning a mask having an aperture adjacent said patch, said aperture defining an area of the sticky surface with which drug substance may come into contact, and in which said portion of the drug substance that becomes stuck to said patch passes through said aperture before coming into contact with said patch.

6. A process according to claim 5 wherein the mask and the substrate are moved relatively into and out of contact with each other so that a part of the mask in which said aperture is located is temporarily in contact with the substrate, drug substance passes through said aperture of the mask when said part of the mask in which the aperture is located is in contact with the substrate, excess drug substance is thereafter removed from the aperture while said part of the mask in which the aperture is located is still in contact with the substrate, and thereafter said part of the mask is separated from the substrate.

7. A process according to claim 5, in which the step of isolating a unit comprising patch and the portion of the drug substance stuck thereto is carried out by cutting a defined area of the substrate at areas free from the sticky substance located between said patches having drug substance stuck to the sticky substance.

8. A process according to claim 7 in which the substrate is in the form of an elongate strip, plural patches of the sticky surface are disposed along at least one of the length and width dimensions of the strip, and the elongate strip is subdivided into units by cutting the substrate at areas free from the sticky substance located between said patches, each said unit including a defined number of said patches after drug substance has become stuck thereto.

9. A process according to claim 1 in which said substrate comprises a substrate base in the form of an elongate strip of flexible material, and patches of a sticky substance on said substrate base, in which said elongate strip is fed continuously along its direction of elongation into a position adjacent a mask, the drug substance is brought into contact with the sticky surface, excess drug substance is removed from the substrate, the substrate is then moved apart from the mask, and thereafter subdivided at areas free from the sticky substance located between said patches to isolate one or more unit of the substrate each unit comprising a defined area of the sticky substance with drug substance stuck thereon.

10. A process according to claim 1, in which said substrate comprises a substrate base in the form of a sheet of flexible material, and patches of a coating of a sticky substance on said substrate base, and on which the substrate is compacted after the sticking of the drug substance thereon.

11. A process according to claim 1 wherein the substrate is compacted by rolling the substrate into a cylinder.

12. A process according to claim 1 wherein the substrate is compacted by folding layers of the substrate to form a stack.

13. A process according to claim 1 wherein the substrate is compacted by stacking isolated units of the substrate together.

* * * * *